(12) United States Patent
Keyomarsi

(10) Patent No.: US 6,218,515 B1
(45) Date of Patent: Apr. 17, 2001

(54) CYCLIN E VARIANTS AND USE THEREOF

(75) Inventor: Khandan Keyomarsi, Rensselaer, NY (US)

(73) Assignee: Health Research, Incorporated, Rensselaer, NY (US)

( * ) Notice: Subject to any disclaimer, the term of this patent is extended or adjusted under 35 U.S.C. 154(b) by 0 days.

(21) Appl. No.: 09/027,007

(22) Filed: Feb. 20, 1998

Related U.S. Application Data

(62) Division of application No. 08/706,539, filed on Sep. 5, 1996, now Pat. No. 5,763,219.
(60) Provisional application No. 60/003,357, filed on Sep. 7, 1995.

(51) Int. Cl.[7] .................................................. C07K 16/00
(52) U.S. Cl. .............................. 530/388.23; 530/387.1; 530/389.2
(58) Field of Search ........................... 530/387.1, 388.23, 530/389.2

(56) References Cited

U.S. PATENT DOCUMENTS

| | | |
|---|---|---|
| 5,449,755 | 9/1995 | Roberts et al. . |
| 5,543,291 | 8/1996 | Keyomarsi et al. . |

FOREIGN PATENT DOCUMENTS

| | | |
|---|---|---|
| WO93/06123 | 4/1993 | (WO) . |

OTHER PUBLICATIONS

Harlow et al. Antibodies a Laboratory Manual, p. 76, Cold Spring Harbor Laboratory, 1988.*
Keyomarsi et al., Proc Natl Acad Sci 90:1112–1116 (1993).
Slingerland et al., Molec Cellular Biol 14(6):3683–3694 (1994).
Kayomarsi et al., Cancer Research 54–380–385 (1994).
Sewing et al., J Cell Science 107:581–588 (1994).
Ohtsubo et al., Molec Cellular Biol 15(5):2612–2624 (1995).
Lew et al., Cell 66:1197–1206 (1991).
Koff et al., Cell 66:1217–1228 (1991).
Lees et al., Genes and Development 6:1874–1885 (1992).
Keyomarsi et al., Oncogene 11:941–950 (1995).
Marx, Science 263:319–321 (1994).

* cited by examiner

*Primary Examiner*—Patrick J. Nolan
(74) *Attorney, Agent, or Firm*—Braman & Rogalskyj, LLP

(57) ABSTRACT

The present invention is directed to nucleic acid molecules encoding a truncated human cyclin E protein, the truncated human cyclin E protein being a constitutively active form of human cyclin E protein. These truncated forms can be encoded by the nucleotide sequence of wild-type cyclin E, with a deletion therein to result in the truncated protein. Vectors and host cells containing the nucleic acid molecules are also provided. The invention further provides isolated fragments of the truncated cyclin E proteins, which fragments consist essentially of the deletion flanking regions of the wild-type cyclin E nucleotide sequence. Antisense nucleic acid molecules, and fragments thereof, to the truncated cyclin E protein and to the fragments thereof are also provided. Methods using the nucleic acid molecules, fragments thereof, antisense nucleic acid molecules, and fragments thereof, are provided. The antisense can be used therapeutically for inhibition of cyclin E activity. An isolated truncated human cyclin E protein is also provided which is a constitutively active form of human cyclin E protein, as well as fragments of the isolated truncated protein. Antibodies to the protein and fragment of the protein are provided, as are compositions comprising the protein and fragment of the protein. Methods using the proteins and fragments of the protein are provided.

3 Claims, 1 Drawing Sheet

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
  (A) LENGTH: 1680 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:1:

```
GTGCTCACCC GGCCCGGTGC CACCCGGGTC CACAGGGATG CGAAGGAGCG GGACACCATG    60
AAGGAGGACG GCGGCGCGGA GTTCTCGGCT CGCTCCAGGA AGAGGAAGGC AAACGTGACC   120
GTTTTTTTGC AGGATCCAGA TGAAGAAATG GCCAAAATCG ACAGGACGGC GAGGGACCAG   180
TGTGGGAGCC AGCCTTGGGA CAATAATGCA GTCTGTGCAG ACCCCTGCTC CCTGATCCCC   240
ACACCTGACA AGAAGATGA TGACCGGGTT TACCCAAACT CAACGTGCAA GCCTCGGATT    300
ATTGCACCAT CCAGAGGCTC CCCGCTGCCT GTACTGAGCT GGGCAAATAG AGAGGAAGTC   360
TGGAAAATCA TGTTAAACAA GGAAAAGACA TACTTAAGGG ATCAGCACTT TCTTGAGCAA   420
CACCCTCTTC TGCAGCCAAA AATGCGAGCA ATTCTTCTGG ATTGGTTAAT GGAGGTGTGT   480
GAAGTCTATA AACTTCACAG GGAGACCTTT TACTTGGCAC AAGATTTCTT TGACCGGTAT   540
ATGGCGACAC AAGAAAATGT TGTAAAAACT CTTTTACAGC TTATTGGGAT TCATCTTTA    600
TTTATTGCAG CCAAACTTGA GGAAATCTAT CCTCCAAAGT TGCACCAGTT TGCGTATGTG   660
ACAGATGGAG CTTGTTCAGG AGATGAAATT CTCACCATG AATTAATGAT TATGAAGGCC    720
CTTAAGTGGC GTTTAAGTCC CCTGACTATT GTGTCCTGGC TGAATGTATA CATGCAGGTT   780
GCATATCTAA ATGACTTACA TGAAGTGCTA CTGCCGCAGT ATCCCCAGCA AATCTTTATA   840
CAGATTGCAG AGCTGTTGGA TCTCTGTGTC CTGGATGTTG ACTGCCTTGA ATTTCCTTAT   900
GGTATACTTG CTGCTTCGGC CTTGTATCAT TTCTCGTCAT CTGAATTGAT GCAAAAGGTT   960
TCAGGGTATC AGTGGTGCGA CATAGAGAAC TGTGTCAAGT GGATGGTTCC ATTTGCCATG  1020
GTTATAAGGG AGACGGGGAG CTCAAAACTG AAGCACTTCA GGGGCGTCGC TGATGAAGAT  1080
GCACACAACA TACAGACCCA CAGAGACAGC TTGGATTTGC TGGACAAAGC CCGAGCAAAG  1140
AAAGCCATGT TGTCTGAACA AAATAGGGCT TCTCCTCTCC CCAGTGGGCT CCTCACCCCG  1200
CCACAGAGCG GTAAGAAGCA GAGCAGCGGG CCGGAAATGG CGTGACCACC CCATCCTTCT  1260
CCACCAAAGA CAGTTGCGCG CCTGCTCCAC GTTCTCTTCT GTCTGTTGCA GCGGAGGCGT  1320
GCGTTTGCTT TTACAGATAT CTGAATGGAA GAGTGTTTCT TCCACAACAG AAGTATTTCT  1380
GTGGATGGCA TCAAACAGGG CAAAGTGTTT TTTATTGAAT GCTTATAGGT TTTTTTTAAA  1440
TAAGTGGGTC AAGTACACCA GCCACCTCCA GACACCAGTG CGTGCTCCCG ATGCTGCTAT  1500
GGAAGGTGCT ACTTGACCTA AAGGACTCCC ACAACAACAA AAGCTTGAAG CTGTGGAGGG  1560
CCACGGTGGC GTGGCTCTCC TCGCAGGTGT TCTGGGCTCC GTTGTACCAA GTGGAGCAGG  1620
TGGTTGCGGG CAAGCGTTGT GCAGAGCCCA TAGCCAGCTG GGCAGGGGGC TGCCCTCTCC  1680
```

(2) INFORMATION FOR SEQ ID NO:2:

```
    (i) SEQUENCE CHARACTERISTICS:
        (A) LENGTH: 1188 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

ATGAAGGAGG ACGGCGGCGC GGAGTTCTCG GCTCGCTCCA GGAAGAGGAA GGCAAACGTG      60

ACCGTTTTTT TGCAGGATCC AGATGAAGAA ATGGCCAAAA TCGACAGGAC GGCGAGGGAC     120

CAGTGTGGGA GCCAGCCTTG GACAATAAT GCAGTCTGTG CAGACCCCTG CTCCCTGATC      180

CCCACACCTG ACAAAGAAGA TGATGACCGG GTTTACCCAA ACTCAACGTG CAAGCCTCGG     240

ATTATTGCAC CATCCAGAGG CTCCCCGCTG CCTGTACTGA GCTGGGCAAA TAGAGAGGAA     300

GTCTGGAAAA TCATGTTAAA CAAGGAAAAG ACATACTTAA GGGATCAGCA CTTTCTTGAG     360

CAACACCCTC TTCTGCAGCC AAAAATGCGA GCAATTCTTC TGGATTGGTT AATGGAGGTG     420

TGTGAAGTCT ATAAACTTCA CAGGGAGACC TTTTACTTGG CACAAGATTT CTTTGACCGG     480

TATATGGCGA CACAAGAAAA TGTTGTAAAA ACTCTTTTAC AGCTTATTGG GATTTCATCT     540

TTATTTATTG CAGCCAAACT TGAGGAAATC TATCCTCCAA AGTTGCACCA GTTTGCGTAT     600

GTGACAGATG GAGCTTGTTC AGGAGATGAA ATTCTCACCA TGGAATTAAT GATTATGAAG     660

GCCCTTAAGT GGCGTTTAAG TCCCCTGACT ATTGTGTCCT GGCTGAATGT ATACATGCAG     720

GTTGCATATC TAAATGACTT ACATGAAGTG CTACTGCCGC AGTATCCCCA GCAAATCTTT     780

ATACAGATTG CAGAGCTGTT GGATCTCTGT GTCCTGGATG TTGACTGCCT TGAATTTCCT     840

TATGGTATAC TTGCTGCTTC GGCCTTGTAT CATTTCTCGT CATCTGAATT GATGCAAAAG     900

GTTTCAGGGT ATCAGTGGTG CGACATAGAG AACTGTGTCA AGTGGATGGT TCCATTTGCC     960

ATGGTTATAA GGGAGACGGG GAGCTCAAAA CTGAAGCACT TCAGGGGCGT CGCTGATGAA    1020

GATGCACACA ACATACAGAC CCACAGAGAC AGCTTGGATT TGCTGGACAA AGCCCGAGCA    1080

AAGAAAGCCA TGTTGTCTGA ACAAAATAGG GCTTCTCCTC TCCCCAGTGG GCTCCTCACC    1140

CCGCCACAGA GCGGTAAGAA GCAGAGCAGC GGGCCGGAAA TGGCGTGA                1188

(2) INFORMATION FOR SEQ ID NO:3:

(i) SEQUENCE CHARACTERISTICS:
        (A) LENGTH: 1179 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATGAAGGAGG ACGGCGGCGC GGAGTTCTCG GCTCGCTCCA GGAAGAGGAA GGCAAACGTG      60

ACCGTTGATC CAGATGAAGA AATGGCCAAA ATCGACAGGA CGGCGAGGGA CCAGTGTGGG     120

AGCCAGCCTT GGGACAATAA TGCAGTCTGT GCAGACCCCT GCTCCCTGAT CCCCACACCT     180

GACAAAGAAG ATGATGACCG GGTTTACCCA AACTCAACGT GCAAGCCTCG GATTATTGCA     240

CCATCCAGAG GCTCCCCGCT GCCTGTACTG AGCTGGGCAA ATAGAGAGGA AGTCTGGAAA     300

ATCATGTTAA ACAAGGAAAA GACATACTTA AGGGATCAGC ACTTTCTTGA GCAACACCCT     360

CTTCTGCAGC CAAAAATGCG AGCAATTCTT CTGGATTGGT TAATGGAGGT GTGTGAAGTC     420

TATAAACTTC ACAGGGAGAC CTTTTACTTG GCACAAGATT TCTTTGACCG GTATATGGCG     480
```

-continued

| | |
|---|---|
| ACACAAGAAA ATGTTGTAAA AACTCTTTTA CAGCTTATTG GGATTTCATC TTTATTTATT | 540 |
| GCAGCCAAAC TTGAGGAAAT CTATCCTCCA AAGTTGCACC AGTTTGCGTA TGTGACAGAT | 600 |
| GGAGCTTGTT CAGGAGATGA AATTCTCACC ATGGAATTAA TGATTATGAA GGCCCTTAAG | 660 |
| TGGCGTTTAA GTCCCCTGAC TATTGTGTCC TGGCTGAATG TATACATGCA GGTTGCATAT | 720 |
| CTAAATGACT TACATGAAGT GCTACTGCCG CAGTATCCCC AGCAAATCTT TATACAGATT | 780 |
| GCAGAGCTGT TGGATCTCTG TGTCCTGGAT GTTGACTGCC TTGAATTTCC TTATGGTATA | 840 |
| CTTGCTGCTT CGGCCTTGTA TCATTTCTCG TCATCTGAAT TGATGCAAAA GGTTTCAGGG | 900 |
| TATCAGTGGT GCGACATAGA GAACTGTGTC AAGTGGATGG TTCCATTTGC CATGGTTATA | 960 |
| AGGGAGACGG GGAGCTCAAA ACTGAAGCAC TTCAGGGGCG TCGCTGATGA AGATGCACAC | 1020 |
| AACATACAGA CCCACAGAGA CAGCTTGGAT TTGCTGGACA AAGCCCGAGC AAAGAAAGCC | 1080 |
| ATGTTGTCTG AACAAAATAG GGCTTCTCCT CTCCCCAGTG GGCTCCTCAC CCCGCCACAG | 1140 |
| AGCGGTAAGA AGCAGAGCAG CGGGCCGGAA ATGGCGTGA | 1179 |

(2) INFORMATION FOR SEQ ID NO:4:

(i) SEQUENCE CHARACTERISTICS:
        (A) LENGTH: 1311 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

| | |
|---|---|
| ATGAAGGAGG ACGGCGGCGC GGAGTTCTCG GCTCGCTCCA GGAAGAGGAA GGCAAACGTG | 60 |
| ACCGTTTTTT TGCAGGATCC AGATGAAGAA ATGGCCAAAA TCGACAGGAC GGCGAGGGAC | 120 |
| CAGTGTGGGA GCCAGCCTTG GACAATAAT GCAGTCTGTG CAGACCCCTG CTCCCTGATC | 180 |
| CCCACACCTG ACAAAGAAGA TGATGACCGG GTTTACCCAA ACTCAACGTG CAAGCCTCGG | 240 |
| ATTATTGCAC CATCCAGAGG CTCCCCGCTG CCTGTACTGA GCTGGGCAAA TAGAGAGGAA | 300 |
| GTCTGGAAAA TCATGTTAAA CAAGGAAAAG ACATACTTAA GGGATCAGCA CTTTCTTGAG | 360 |
| CAACACCCTC TTCTGCAGCC AAAAATGCGA GCAATTCTTC TGGATTGGTT AATGGAGGTG | 420 |
| TGTGAAGTCT ATAAACTTCA CAGGGAGACC TTTTACTTGG CACAAGATTT CTTTGACCGG | 480 |
| TATATGCGA CACAAGAAAA TGTTGTAAAA ACTCTTTTAC AGCTTATTGG GATTTCATCT | 540 |
| TTATTTATTG CAGCCAAACT TGAGGAAATC TATCCTCCAA AGTTGCACCA GTTTGCGTAT | 600 |
| GTGACAGATG GAGCTTGTTC AGGAGATGAA ATTCTCACCA TGGAATTAAT GATTATGAAG | 660 |
| GCCCTTAAGT GGCGTTTAAG TCCCCTGACT ATTGTGTCCT GGCTGAATGT ATACATGCAG | 720 |
| GTTGCATATC TAAATGACTT ACATGAAGTG CTACTGCCGC AGTATCCCCA GCAAATCTTT | 780 |
| ATACAGATTG CAGAGCTGTT GGATCTCTGT GTCCTGGATG TTGACTGCCT TGAATTTCCT | 840 |
| TATGGTATAC TTGCTGCTTC GGCCTTGTAT CATTTCTCGT CATCTGAATT GATGCAAAAG | 900 |
| GTTTCAGGGT ATCAGTGGTG CGACATAGAG AACTGTGTCA AGTGGATGGT TCCATTTGCC | 960 |
| ATGGTTATAA GGGAGACGGG GAGCTCAAAA CTGAAGCACA GAGCGGTAAG AAGCAGAGCA | 1020 |
| GCGGGCCGGA AATGGCGTGA CCACCCCATC CTTCTCCACC AAAGACAGTT GCGCGCCTGC | 1080 |
| TCCACGTTCT CTTCTGTCTG TTGCAGCGGA GGCGTGCGTT TGCTTTTACA GATATCTGAA | 1140 |
| TGGAAGAGTG TTTCTTCCAC AACAGAAGTA TTTCTGTGGA TGGCATCAAA CAGGGCAAAG | 1200 |
| TGTTTTTTAT TGAATGCTTA TAGGTTTTTT TTAAATAAGT GGGTCAAGTA CACCAGCCAC | 1260 |

CTCCAGACAC CAGTGCGTGC TCCCGATGCT GCTATGGAAG GTGCTACTTG A            1311

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGGATGCGAA GGAGCGGGAC A                                              21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGCGGCGCAA CTGTCTTTGG T                                              21

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCAAACGTGA CCGTTG                                                    16

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ACCGCTCTGT GCTTCATC                                                  18

(2) INFORMATION FOR SEQ ID NO:9:

(i) SEQUENCE CHARACTERISTICS:
        (A) LENGTH: 392 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

Met Lys Glu Asp Gly Gly Ala Glu Phe Ser Ala Arg Ser Arg Lys Arg
1               5                   10                  15

Lys Ala Asn Val Thr Val Asp Pro Asp Glu Glu Met Ala Lys Ile Asp

```
                    20                  25                  30
Arg Thr Ala Arg Asp Gln Cys Gly Ser Gln Pro Trp Asp Asn Asn Ala
                35                  40                  45

Val Cys Ala Asp Pro Cys Ser Leu Ile Pro Thr Pro Asp Lys Glu Asp
 50                  55                  60

Asp Asp Arg Val Tyr Pro Asn Ser Thr Cys Lys Pro Arg Ile Ile Ala
 65                  70                  75                  80

Pro Ser Arg Gly Ser Pro Leu Pro Val Leu Ser Trp Ala Asn Arg Glu
                 85                  90                  95

Glu Val Trp Lys Ile Met Leu Asn Lys Glu Lys Thr Tyr Leu Arg Asp
                100                 105                 110

Gln His Phe Leu Glu Gln His Pro Leu Leu Gln Pro Lys Met Arg Ala
            115                 120                 125

Ile Leu Leu Asp Trp Leu Met Glu Val Cys Glu Val Tyr Lys Leu His
        130                 135                 140

Arg Glu Thr Phe Tyr Leu Ala Gln Asp Phe Phe Asp Arg Tyr Met Ala
145                 150                 155                 160

Thr Gln Glu Asn Val Val Lys Thr Leu Leu Gln Leu Ile Gly Ile Ser
                165                 170                 175

Ser Leu Phe Ile Ala Ala Lys Leu Glu Glu Ile Tyr Pro Pro Lys Leu
            180                 185                 190

His Gln Phe Ala Tyr Val Thr Asp Gly Ala Cys Ser Gly Asp Glu Ile
        195                 200                 205

Leu Thr Met Glu Leu Met Ile Met Lys Ala Leu Lys Trp Arg Leu Ser
    210                 215                 220

Pro Leu Thr Ile Val Ser Trp Leu Asn Val Tyr Met Gln Val Ala Tyr
225                 230                 235                 240

Leu Asn Asp Leu His Glu Val Leu Leu Pro Gln Tyr Pro Gln Gln Ile
                245                 250                 255

Phe Ile Gln Ile Ala Glu Leu Leu Asp Leu Cys Val Leu Asp Val Asp
            260                 265                 270

Cys Leu Glu Phe Pro Tyr Gly Ile Leu Ala Ala Ser Ala Leu Tyr His
        275                 280                 285

Phe Ser Ser Ser Glu Leu Met Gln Lys Val Ser Gly Tyr Gln Trp Cys
    290                 295                 300

Asp Ile Glu Asn Cys Val Lys Trp Met Val Pro Phe Ala Met Val Ile
305                 310                 315                 320

Arg Glu Thr Gly Ser Ser Lys Leu Lys His Phe Arg Gly Val Ala Asp
                325                 330                 335

Glu Asp Ala His Asn Ile Gln Thr His Arg Asp Ser Leu Asp Leu Leu
            340                 345                 350

Asp Lys Ala Arg Ala Lys Lys Ala Met Leu Ser Glu Gln Asn Arg Ala
        355                 360                 365

Ser Pro Leu Pro Ser Gly Leu Leu Thr Pro Pro Gln Ser Gly Lys Lys
    370                 375                 380

Gln Ser Ser Gly Pro Glu Met Ala
385                 390
```

(2) INFORMATION FOR SEQ ID NO:10:

(i) SEQUENCE CHARACTERISTICS:
        (A) LENGTH: 436 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

| | | | | | | | | | | | | | | |
|---|---|---|---|---|---|---|---|---|---|---|---|---|---|---|
| Met | Lys | Glu | Asp | Gly | Gly | Ala | Glu | Phe | Ser | Ala | Arg | Ser | Arg | Lys | Arg |
| 1 | | | | 5 | | | | | 10 | | | | | 15 | |
| Lys | Ala | Asn | Val | Thr | Val | Phe | Leu | Gln | Asp | Pro | Asp | Glu | Glu | Met | Ala |
| | | | 20 | | | | | 25 | | | | | 30 | | |
| Lys | Ile | Asp | Arg | Thr | Ala | Arg | Asp | Gln | Cys | Gly | Ser | Gln | Pro | Trp | Asp |
| | | | 35 | | | | | 40 | | | | | 45 | | |
| Asn | Asn | Ala | Val | Cys | Ala | Asp | Pro | Cys | Ser | Leu | Ile | Pro | Thr | Pro | Asp |
| | 50 | | | | | 55 | | | | | 60 | | | | |
| Lys | Glu | Asp | Asp | Asp | Arg | Val | Tyr | Pro | Asn | Ser | Thr | Cys | Lys | Pro | Arg |
| 65 | | | | | 70 | | | | | 75 | | | | | 80 |
| Ile | Ile | Ala | Pro | Ser | Arg | Gly | Ser | Pro | Leu | Pro | Val | Leu | Ser | Trp | Ala |
| | | | | 85 | | | | | 90 | | | | | 95 | |
| Asn | Arg | Glu | Glu | Val | Trp | Lys | Ile | Met | Leu | Asn | Lys | Glu | Lys | Thr | Tyr |
| | | | | 100 | | | | | 105 | | | | | 110 | |
| Leu | Arg | Asp | Gln | His | Phe | Leu | Glu | Gln | His | Pro | Leu | Leu | Gln | Pro | Lys |
| | | | 115 | | | | | 120 | | | | | 125 | | |
| Met | Arg | Ala | Ile | Leu | Leu | Asp | Trp | Leu | Met | Glu | Val | Cys | Glu | Val | Tyr |
| | | | 130 | | | | | 135 | | | | | 140 | | |
| Lys | Leu | His | Arg | Glu | Thr | Phe | Tyr | Leu | Ala | Gln | Asp | Phe | Phe | Asp | Arg |
| 145 | | | | | 150 | | | | | 155 | | | | | 160 |
| Tyr | Met | Ala | Thr | Gln | Glu | Asn | Val | Val | Lys | Thr | Leu | Leu | Gln | Leu | Ile |
| | | | | 165 | | | | | 170 | | | | | 175 | |
| Gly | Ile | Ser | Ser | Leu | Phe | Ile | Ala | Ala | Lys | Leu | Glu | Glu | Ile | Tyr | Pro |
| | | | 180 | | | | | 185 | | | | | 190 | | |
| Pro | Lys | Leu | His | Gln | Phe | Ala | Tyr | Val | Thr | Asp | Gly | Ala | Cys | Ser | Gly |
| | | | 195 | | | | | 200 | | | | | 205 | | |
| Asp | Glu | Ile | Leu | Thr | Met | Glu | Leu | Met | Ile | Met | Lys | Ala | Leu | Lys | Trp |
| | | 210 | | | | | 215 | | | | | 220 | | | |
| Arg | Leu | Ser | Pro | Leu | Thr | Ile | Val | Ser | Trp | Leu | Asn | Val | Tyr | Met | Gln |
| 225 | | | | | 230 | | | | | 235 | | | | | 240 |
| Val | Ala | Tyr | Leu | Asn | Asp | Leu | His | Glu | Val | Leu | Leu | Pro | Gln | Tyr | Pro |
| | | | | 245 | | | | | 250 | | | | | 255 | |
| Gln | Gln | Ile | Phe | Ile | Gln | Ile | Ala | Glu | Leu | Leu | Asp | Leu | Cys | Val | Leu |
| | | | 260 | | | | | 265 | | | | | 270 | | |
| Asp | Val | Asp | Cys | Leu | Glu | Phe | Pro | Tyr | Gly | Ile | Leu | Ala | Ala | Ser | Ala |
| | | 275 | | | | | 280 | | | | | 285 | | | |
| Leu | Tyr | His | Phe | Ser | Ser | Glu | Leu | Met | Gln | Lys | Val | Ser | Gly | Tyr |
| | 290 | | | | | 295 | | | | | 300 | | | | |
| Gln | Trp | Cys | Asp | Ile | Glu | Asn | Cys | Val | Lys | Trp | Met | Val | Pro | Phe | Ala |
| 305 | | | | | 310 | | | | | 315 | | | | | 320 |
| Met | Val | Ile | Arg | Glu | Thr | Gly | Ser | Ser | Lys | Leu | Lys | His | Arg | Ala | Val |
| | | | | 325 | | | | | 330 | | | | | 335 | |
| Arg | Ser | Arg | Ala | Ala | Gly | Arg | Lys | Trp | Arg | Asp | His | Pro | Ile | Leu | Leu |
| | | | 340 | | | | | 345 | | | | | 350 | | |
| His | Gln | Arg | Gln | Leu | Arg | Ala | Cys | Ser | Thr | Phe | Ser | Ser | Val | Cys | Cys |
| | | | 355 | | | | | 360 | | | | | 365 | | |
| Ser | Gly | Gly | Val | Arg | Leu | Leu | Leu | Gln | Ile | Ser | Glu | Trp | Lys | Ser | Val |
| | | 370 | | | | | 375 | | | | | 380 | | | |
| Ser | Ser | Thr | Thr | Glu | Val | Phe | Leu | Trp | Met | Ala | Ser | Asn | Arg | Ala | Lys |
| 385 | | | | | 390 | | | | | 395 | | | | | 400 |

```
Cys Phe Leu Leu Asn Ala Tyr Arg Phe Phe Leu Asn Lys Trp Val Lys
                405                 410                 415
Tyr Thr Ser His Leu Gln Thr Pro Val Arg Ala Pro Asp Ala Ala Met
            420                 425                 430
Glu Gly Ala Thr
        435
```

(2) INFORMATION FOR SEQ ID NO:11:

(i) SEQUENCE CHARACTERISTICS:
        (A) LENGTH: 395 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

```
Met Lys Glu Asp Gly Gly Ala Glu Phe Ser Ala Arg Ser Arg Lys Arg
1               5                   10                  15
Lys Ala Asn Val Thr Val Phe Leu Gln Asp Pro Asp Glu Glu Met Ala
                20                  25                  30
Lys Ile Asp Arg Thr Ala Arg Asp Gln Cys Gly Ser Gln Pro Trp Asp
            35                  40                  45
Asn Asn Ala Val Cys Ala Asp Pro Cys Ser Leu Ile Pro Thr Pro Asp
        50                  55                  60
Lys Glu Asp Asp Asp Arg Val Tyr Pro Asn Ser Thr Cys Lys Pro Arg
65                  70                  75                  80
Ile Ile Ala Pro Ser Arg Gly Ser Pro Leu Pro Val Leu Ser Trp Ala
                85                  90                  95
Asn Arg Glu Glu Val Trp Lys Ile Met Leu Asn Lys Glu Lys Thr Tyr
                100                 105                 110
Leu Arg Asp Gln His Phe Leu Glu Gln His Pro Leu Leu Gln Pro Lys
            115                 120                 125
Met Arg Ala Ile Leu Leu Asp Trp Leu Met Glu Val Cys Glu Val Tyr
        130                 135                 140
Lys Leu His Arg Glu Thr Phe Tyr Leu Ala Gln Asp Phe Phe Asp Arg
145                 150                 155                 160
Tyr Met Ala Thr Gln Glu Asn Val Val Lys Thr Leu Gln Leu Ile
                165                 170                 175
Gly Ile Ser Ser Leu Phe Ile Ala Ala Lys Leu Glu Glu Ile Tyr Pro
                180                 185                 190
Pro Lys Leu His Gln Phe Ala Tyr Val Thr Asp Gly Ala Cys Ser Gly
            195                 200                 205
Asp Glu Ile Leu Thr Met Glu Leu Met Ile Met Lys Ala Leu Lys Trp
        210                 215                 220
Arg Leu Ser Pro Leu Thr Ile Val Ser Trp Leu Asn Val Tyr Met Gln
225                 230                 235                 240
Val Ala Tyr Leu Asn Asp Leu His Glu Val Leu Leu Pro Gln Tyr Pro
                245                 250                 255
Gln Gln Ile Phe Ile Gln Ile Ala Glu Leu Leu Asp Leu Cys Val Leu
            260                 265                 270
Asp Val Asp Cys Leu Glu Phe Pro Tyr Gly Ile Leu Ala Ala Ser Ala
        275                 280                 285
Leu Tyr His Phe Ser Ser Ser Glu Leu Met Gln Lys Val Ser Gly Tyr
    290                 295                 300
```

-continued

```
Gln Trp Cys Asp Ile Glu Asn Cys Val Lys Trp Met Val Pro Phe Ala
305                 310                 315                 320

Met Val Ile Arg Glu Thr Gly Ser Ser Lys Leu Lys His Phe Arg Gly
                325                 330                 335

Val Ala Asp Glu Asp Ala His Asn Ile Gln Thr His Arg Asp Ser Leu
                340             345                 350

Asp Leu Leu Asp Lys Ala Arg Ala Lys Lys Ala Met Leu Ser Glu Gln
        355                 360                 365

Asn Arg Ala Ser Pro Leu Pro Ser Gly Leu Leu Thr Pro Pro Gln Ser
    370             375                 380

Gly Lys Lys Gln Ser Ser Gly Pro Glu Met Ala
385             390             395
```

CYCLIN E VARIANTS AND USE THEREOF

This application is a divisional of U.S. Ser. No. 08/706,539, filed Sep. 5, 1996, which issued as U.S. Pat. No. 5,763,219 on Jun. 9, 1998 priority of U.S. Provisional Patent Application No. 60/003,357, filed Sep. 7, 1995.

The subject matter of this application was made with support from the United States Government under Department of Defense Grant No. DAMD-17-94-J-4081, AIBS # 1579 from the U.S. Army Medical Research Acquisition Activity.

FIELD OF THE INVENTION

The present invention relates generally to cyclin E variants, and more particularly to constitutively active truncated human cyclin E proteins and uses thereof.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Cyclins are prime cell cycle regulators and central to the control of cell proliferation in eukaryotic cells via their association with and activation of cyclin-dependent protein kinases 1–7 (cdks) (reviewed in, Elledge et al., 1991; Heichman et al., 1994; Hunter et al., 1994; King et al., 1994; Morgan, 1995; Nurse, 1994; Sherr, 1994). Cyclins were first identified in marine invertebrates as a result of their dramatic cell cycle expression patterns during meiotic and early mitotic divisions (Evans et al., 1983; Sherr, 1993; Standart et al., 1987; Swenson et al., 1986). Several classes of cyclins have been described and are currently designated as cyclins A–H, some with multiple members (reviewed in Draetta, 1994). Cyclins can be distinguished on the basis of conserved sequence motifs, patterns of appearance and apparent functional roles during specific phases and regulatory points of the cell cycle in a variety of species.

The connection between cyclins and cancer has been substantiated with the D type cyclins (Draetta, 1994; Hunter et al., 1991; Hunter & Pines, 1994; Sherr, 1993). Cyclin D1 was identified simultaneously by several laboratories using independent systems: It was identified in mouse macrophages due to its induction by colony stimulating factor 1 during G1 (Matsushime et al., 1991); in complementation studies using yeast strains deficient in G1 cyclins (Lew et al., 1991; Xiong et al., 1991); as the product of the bcl-1 oncogene (Withers et al., 1991), and as the PRAD1 proto-oncogene in some parathyroid tumors where its locus is overexpressed as a result of a chromosomal rearrangement that translocates it to the enhancer of the parathyroid hormone gene (Matsushime, et al., 1991; Motokura et al., 1993; Motokura et al., 1991; Quelle et al., 1993). In centrocytic B cell lymphomas cyclin D1 (PRAD1)/BCL1 is targeted by chromosomal translocations at the BCL1 breakpoint, t(11;14)(q13;q32) (Rosenberg et al., 1991a; Rosenberg et al., 1991b). Furthermore, the cyclin D1 locus undergoes gene amplification in mouse skin carcinogenesis, as well as in breast, esophageal, colorectal and squamous cell carcinomas (Bianchi et al., 1993; Buckley et al., 1993; Jiang et al., 1992; Jiang et al., 1993b; Lammie et al., 1991; Leach et al., 1993). Several groups have examined the ability of cyclin D1 to transform cells directly in culture with mixed results (Hinds et al., 1994; Hinds et al., 1992; Jiang et al., 1993a; Lovec et al., 1994; Musgrove et al., 1994; Quelle, et al., 1993; Resnitzky et al., 1994; Rosenwald et al., 1993; Sherr, 1993). However, the overexpression of cyclin D1 was recently observed in mammary cells of transgenic mice and results in abnormal proliferation of these cells and the development of mammary adenocarcinomas (Wang et al., 1994). This observation strengthens the hypothesis that the inappropriate expression of a G1 type cyclin may lead to loss of growth control.

Recently, the linkage between oncogenesis and the cell cycle has been reinforced by correlating the deranged expression of cyclins to the loss of growth control in breast cancer (Buckley, et al., 1993; Keyomarsi et al., 1993). Using proliferating normal versus human tumor breast cell lines in culture as a model system, several changes that are seen in all or most of these lines have been described. These include increased cyclin mRNA stability, resulting in overexpression of mitotic cyclins and cdk2 RNAs and proteins in 9/10 tumor lines, leading to the deranged order of appearance of mitotic cyclins prior to Gi cyclins in synchronized tumor cells.

The most striking abnormality in cyclin expression found was that of cyclin E. Cyclin E protein not only was overexpressed in 10/10 breast tumor cell lines but it was also present in lower molecular weight isoforms than that found in normal cells (Keyomarsi & Pardee, 1993). One possibility for the presence of multiple transcripts of cyclin E is due to alternative splicing. Precedent for alternative splicing of cyclin E has recently been reported by Ohtsubo et. al. where they identified a longer form of cyclin E (cyclin E–L) which contains 15 amino acids at the amino terminus which through alternative splicing, is absent in the original form of cyclin E (cyclin E wt) (Ohtsubo et al., 1995). In addition Sewing et al. also identified another splice variant of cyclin E, termed cyclin Es (Sewing et al., 1994). Cyclin Es lacks 49 amino acids within the cyclin box, and is 90% less abundant than the wild-type cyclin E sequence. This form is unable to associate with cdk2, is inactive in histone H1 kinase assays, and is unable to rescue a triple CLN mutation of S. cerevisiae (Sewing, et al., 1994). The cyclin box is a consensus region which confers activity by its association to a cdk (Lees et al., 1992). The relevance of cyclin derangement to in vivo conditions was directly examined, by measuring the expression of cyclin E protein in tumor samples versus normal adjacent tissue obtained from patients with various malignancies (Keyomarsi et al., 1994). These analyses revealed that breast cancers and other solid tumors, as well as malignant lymphocytes from patients with lymphatic leukemia, show severe quantitative and qualitative alteration in cyclin E protein expression independent of the S-phase fraction of the samples. In addition, the alteration of cyclin E becomes more severe with breast tumor stage and grade and is more consistent than cell proliferation or other tumor markers such as PCNA or c-erb B2. These observations strongly suggested the use of cyclin E as a new prognostic marker.

Therefore, a need exists to further characterize the alterations of cyclin E in breast cancer.

SUMMARY OF INVENTION

To this end, the subject invention shows that while cyclin E is cell cycle regulated in normal cells, it is present constitutively and in an active cdk2 complex in synchronized populations of breast cancer cells. Two truncated variant forms of cyclin E mRNA are detected by RT-PCR, which are ubiquitously detected in normal and tumor cells and tissues. These variant forms of cyclin E can give rise to an active cyclin/cdk2 complex in vitro, but they do not seem to be translated in normal cells.

It is an object of the subject invention to identify truncated human cyclin E protein forms which are constitutively active. It is a further object of the subject invention to provide DNA and amino acid sequences of these truncated forms of human cyclin E protein, so that the DNA sequence can be used to devise antisense nucleic acid (for use in blocking translation of mRNA encoding the truncated human cyclin E protein forms, thereby decreasing expression of the truncated human cyclin E protein forms in cells), and so that the amino acid sequence can be used to construct fragments of the truncated human cyclin E protein forms (for production of antibody to the truncated human cyclin E protein form, which can be used for detection of the truncated form).

In accordance with these objectives, the subject invention provides an isolated nucleic acid molecule encoding a truncated human cyclin E protein, the truncated human cyclin E protein being a constitutively active form of human cyclin E protein. The invention also provides an antisense nucleic acid molecule complementary to the mRNA encoding the truncated human cyclin E protein, or a fragment thereof capable of hybridizing under stringent conditions to the mRNA.

The invention further provides an isolated fragment of the nucleic acid molecule encoding the truncated human cyclin E protein. Preferably, the truncated forms of human cyclin E protein are encoded by DNA having a deletion in the nucleotide sequence for wild-type human cyclin E, and the fragment of the nucleic acid molecule of the subject invention consists essentially of a nucleotide sequence located 5' to the deletion adjacent to a nucleotide sequence located 3' to the deletion. Antisense nucleic acid molecules to these fragments are also provided.

The nucleic acid molecules of the invention can be inserted into suitable expression vectors and/or host cells. Expression of the nucleic acid molecules encoding the truncated human cyclin E proteins results in production of truncated human cyclin E proteins. Expression of the antisense nucleic acid molecules or fragments thereof results in decreased expression of the truncated human cyclin E proteins. Decreased expression of the truncated human cyclin E proteins can also be accomplished by exposing a cell to a drug that functionally mimics the antisense molecules (wherein the drug blocks the translation of the mRNA).

The invention also provides an isolated truncated human cyclin E protein, the truncated human cyclin E protein being a constitutively active form of human cyclin E protein, and antibodies or antibody fragments specific for the truncated human cyclin E protein.

Fragments of the truncated human cyclin E protein are further provided, wherein (as with the nucleic acid molecules encoding the truncated proteins) the fragment of the protein consists essentially of amino acids encoded by the nucleotide sequence located 5' to the deletion adjacent to amino acids encoded by the nucleotide sequence located 3' to the deletion. Antibodies or antibody fragments specific to the fragments of the truncated protein are provided.

The antibodies and antibody fragments can be used to detect the presence of the truncated human cyclin E proteins in samples.

With the identification of the cyclin E variants that may be translated in tumor but not normal cells, the oncogenecity of these cyclin E forms can be directly deciphered. The identification of the cyclin E variants also allows the variant forms to be utilized as molecular probes to identify their protein products in tumor cells and tissues. Identification of the multiple protein isoforms of cyclin E provides insight as to the regulation of cyclin E, which when complexed with-cdk2 is thought to be rate limiting for the G1/S transition during the mammalian cell cycle. With an active cyclin E/cdk2 complex, substrates may be phosphorylated at altered points in the cell cycle resulting in loss of checkpoint control during the progression of G1 to S in tumor cells.

BRIEF DESCRIPTION OF THE DRAWINGS

These and other features and advantages of this invention will be evident from the following detailed description of preferred embodiments when read in conjunction with the accompanying drawing in which.

DETAILED DESCRIPTION

Figure 1:
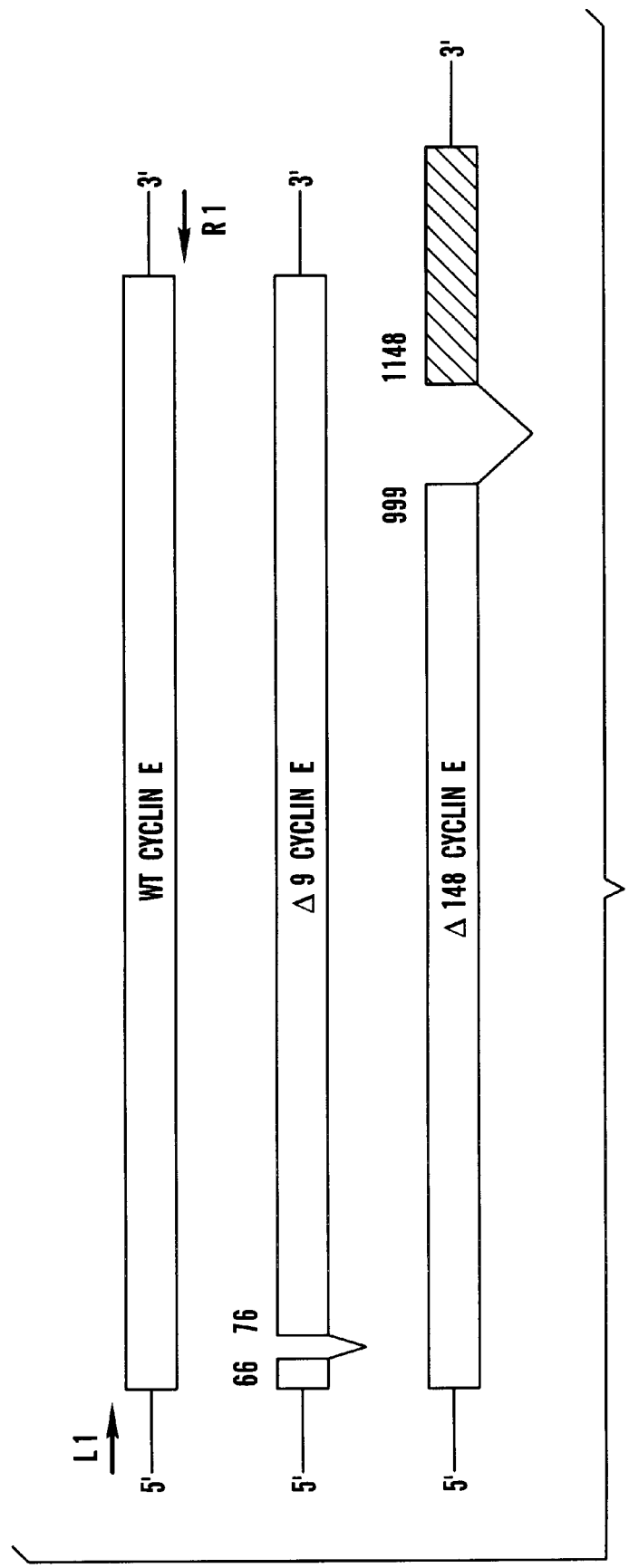
FIG. 1 shows the relative position of cyclin E Δ9 and Δ148 deletions to the wild-type cyclin E sequence. The two arrows flanking the cyclin E coding region refer to the position of R1 (i.e., R1CYCE) and L1 (i.e., L1CYCE) oligonucleotides used for the RT-PCR reactions.

The subject invention provides an isolated nucleic acid molecule encoding a truncated human cyclin E protein, the truncated human cyclin E protein being a constitutively active form of human cyclin E protein. The nucleic acid molecule can be deoxyribonucleic acid (DNA) or ribonucleic acid (RNA), genomic or recombinant, biologically isolated or synthetic. The DNA molecule can be a cDNA molecule, which is a DNA copy of a messenger RNA (mRNA) encoding the truncated human cyclin E protein. The RNA molecule can be mRNA.

In one embodiment, the truncated human cyclin E protein is encoded by cDNA having a deletion in the nucleotide sequence as shown in SEQ ID NO:1. SEQ ID NO:1 is the DNA sequence of wild-type cyclin E cDNA, as published by Koff et al., including the 5' and 3' non-coding regions. SEQ ID NO:2 is the DNA sequence of wild-type cyclin E cDNA, again as published by Koff et al., for just the coding region (including the start and stop codons). The amino acid sequence of wild-type cyclin E, as published by Koff et al., is shown in SEQ ID NO:11.

One embodiment of a truncated human cyclin E protein of the subject invention is encoded by cDNA having a deletion consisting essentially of nucleotides 124–132 of SEQ ID NO:1 (which are nucleotides 67–75 of the coding region as shown in SEQ ID NO:2). This form of truncated cyclin E is referred to herein as cyclin E Δ9, since 9 nucleotides are deleted. Cyclin E Δ9 has a nucleotide sequence as shown in SEQ ID NO:3. Cyclin E Δ9 has an amino acid sequence as shown in SEQ ID NO:9. Three amino acids are deleted from the wild-type cyclin E protein to result in cyclin E Δ9. Those amino acids are residues 23 to 25 of SEQ ID NO:11. This deletion does not alter the reading frame of the encoded protein, and cyclin E Δ9 has the same stop codon position as wild type cyclin E.

A further embodiment of a truncated human cyclin E protein of the subject invention is encoded by cDNA having a deletion consisting essentially of nucleotides 1057–1204 of SEQ ID NO:1 (which are nucleotides 1000–1147 of the coding region as shown in SEQ ID NO:2). This form of truncated cyclin E is referred to herein as cyclin E Δ148, since 148 nucleotides are deleted. The deletion causes a shift in the reading frame of the encoded protein, resulting in a change in the position of the stop codon for cyclin E Δ148. The nucleotide sequence of cyclin E Δ148 thus extends into the 3' non-coding region of the wild-type cyclin E shown in SEQ ID NO:1. Cyclin E Δ148 thus has a nucleotide sequence as shown in SEQ ID NO:4. Cyclin E Δ148 has an amino acid sequence as shown in SEQ ID NO:10. Forty-nine complete codons are deleted from the wild-type cyclin E sequence (49 amino acids, residues 333–381 of SEQ ID NO:11), and the additional single nucleotide deletion results-in a reading frame shift. The cyclin E Δ148 therefore has a stop codon which is at nucleotide position 1514–1516 in the sequence of wild-type cyclin E shown in SEQ ID NO:1.

The invention also provides an antisense nucleic acid molecule that is complementary to the mRNA encoding the truncated human cyclin E protein, or a fragment thereof capable of hybridizing under stringent conditions to the mRNA. The antisense nucleic acid molecule is ribonucleic acid. This antisense molecule can base-pair with the mRNA, preventing translation of the mRNA into protein.

The invention further provides an isolated fragment of the nucleic acid molecule encoding the truncated human cyclin E protein. The truncated cyclin E protein is encoded by cDNA having a deletion in the nucleotide sequence as shown in SEQ ID NO:1 (the wild-type cyclin E nucleotide sequence), and the fragments of the subject invention consist essentially of a nucleotide sequence located 5' to the deletion adjacent (in the 5' to 3' order) to a nucleotide sequence located 3' to the deletion (i.e., the fragment consists essentially of sequences flanking the deletion). The fragments preferably comprise about 10 to about 30 nucleotides, with about 5 to about 15 nucleotides from each of the 5' flanking region and the 3' flanking region. More preferable fragments comprise about 20 to about 30 nucleotides, with about 5 to about 15 nucleotides from each of the 5' flanking region and the 3' flanking region.

Antisense nucleic acid molecules to these fragments are also provided. The antisense nucleic acid molecules are complementary to the mRNA of the fragment. Having identified antisense nucleic acid molecules to fragments of the truncated cyclin E proteins, drugs can be made which functionally mimic the antisense nucleic acid molecules (i.e. the drugs block translation of mRNA encoding the truncated cyclin E proteins). Such drugs include peptide drugs, and can also be used to decrease expression of truncated cyclin E proteins.

Nucleic acid molecules encoding truncated human cyclin E proteins, and fragments of the nucleic acid molecules, are thus provided. Antisense nucleic acid molecules (or fragments thereof) to the nucleic acid molecules encoding the "full-length" truncated proteins as well as to the fragments of the nucleic acid molecules, are also provided.

Each of the nucleic acid molecules, fragments thereof, antisense nucleic acid molecules, and fragments thereof, can be expressed in suitable host cells using conventional techniques. Such techniques may involve the use of expression vectors which comprise the nucleic acid molecules, fragments thereof, antisense nucleic acid molecules, or fragments thereof. These expression vectors can then be used to transform suitable host cells.

Host cells transformed with nucleic acid molecules encoding the truncated human cyclin E proteins can be used to produce the truncated proteins (or cells transformed with the fragments can be used to produce fragments of the truncated proteins). Alternatively, the fragments or full-length truncated proteins can be produced synthetically using the sequence information of the truncated proteins and fragments. In host cells transformed with the antisense nucleic acid molecules, or fragments thereof, the antisense nucleic acid molecules or fragments thereof will block translation of the truncated cyclin E protein. Accordingly, in host cells transformed with the antisense nucleic acid molecules or fragments thereof, the expression of truncated cyclin E proteins is decreased.

The invention further provides isolated truncated human cyclin E proteins, the truncated human cyclin E proteins being a constitutively active form of human cyclin E protein. These truncated proteins are encoded by a nucleotide sequence having a deletion in the nucleotide sequence as shown in SEQ ID NO:1 (the nucleotide sequence for wild-type cyclin E, including the 5' and 3' non-coding regions). In one embodiment, cyclin E Δ9, the truncated human cyclin E is encoded by an amino acid sequence as shown in SEQ ID NO:9. In another embodiment, cyclin E Δ148, the truncated human cyclin E is encoded by an amino acid sequence as shown in SEQ ID NO:10.

Isolated fragments of the truncated cyclin E proteins are also provided, wherein the fragment consists essentially of amino acids encoded by a nucleotide sequence located 5' to the deletion adjacent (5' to 3') to amino acids encoded by a nucleotide sequence located 3' to the deletion. Preferably, the fragment consists of about 3 to about 10 amino acids.

Each of the truncated cyclin E proteins, and the isolated fragments thereof, can be provided in a comprising the truncated protein or fragment thereof and a compatible carrier.

Antibodies can also be raised to each of the truncated cyclin E proteins, and to the isolated fragments thereof. Antibodies of the subject invention include polyclonal antibodies and monoclonal antibodies which are specific for the truncated cyclin E proteins or isolated fragments thereof. It is known in the art that fragments of such antibodies can also be used to bind to the truncated proteins or fragments thereof. These antibodies or fragments thereof can thus be used to detect the presence of a truncated cyclin E form in a sample (or to detect the presence of a fragment of a truncated cyclin E form), by contacting the sample with the antibody or fragment thereof. The antibody or fragment thereof binds to any truncated cyclin E protein or fragment thereof present in the sample, forming a complex therewith. The complex can then be detected, thereby detecting the presence of the truncated cyclin E protein or fragment thereof in the sample.

As used herein, a nucleic acid molecule encoding a truncated human cyclin E protein has a nucleotide sequence which is at least 90% homologous to the nucleotide sequence of wild-type human cyclin E (as shown in SEQ ID NO:1 or SEQ ID NO:2, i.e. with or without the non-coding regions), except for a region which is deleted. More particularly, the truncated human cyclin E has a nucleotide sequence reading from the 5' to 3' direction which is at least 90% homologous to the nucleotide sequence of wild-type human cyclin E, again reading from the 5' to 3' direction, until the deletion is reached. The truncated human cyclin E then has a nucleotide sequence reading from the 3' to 5' direction which is at least 90% homologous to the nucleotide sequence of wild-type human cyclin E, again reading from the 3' to 5' direction, until the deletion is reached from the opposite end of the molecule. Thus, the nucleotide sequence of the truncated human cyclin E according to the subject invention actually comprises two sequences which are at least 90% homologous (nucleotide) to the regions of DNA encoding wild-type human cyclin E flanking the site of the deletion.

While the nucleotide sequence is at least 90% homologous, nucleotide identity is not required. As should be readily apparent to those skilled in the art, various nucleotide substitutions are possible which are silent mutations (i.e. the amino acid encoded by the particular codon does not change). It is also possible to substitute a nucleotide which alters the amino acid encoded by a particular codon, where the amino acid substituted is a conservative substitution (i.e. amino acid "homology" is conserved). It is also possible to have minor nucleotide and/or amino acid additions, deletions, and/or substitutions in the wild-type human cyclin E nucleotide and/or amino acid sequences which do not alter the function of the resulting cyclin E.

The nucleic acid molecules of the subject invention are identified as those encoding a constitutively active, truncated form of wild-type human cyclin E. A deletion results in the protein encoded by the nucleic acid molecule being shorter than wild-type cyclin E protein, i.e. the protein is truncated. The resulting truncated cyclin E protein is constitutively active, in that it is present in a complex with cdk2 throughout a cell cycle. In order to be constitutively active, the deletion in the nucleotide sequence of the wild-type human cyclin E cannot occur within the cyclin box domain, generally considered to be between nucleotides 379–777 (as shown in SEQ ID NO:1), with the actual cyclin binding region considered to be nucleotides 379–431 and 634–777 (as shown in SEQ ID NO:1). Therefore, while it is preferably to delete nucleotides outside the 379–777 region, mutations may be possible within the 432–633 region without adversely affecting the activity of the resulting cyclin E.

The deletion should be at least 9 nucleotides (such as cyclin E Δ9) and can be up to 500 nucleotides (which represents a deletion of about 20 KD). While the examples herein are of truncated cyclin E forms that have a continuous deletion, it is also possible to obtain truncated forms wherein a non-continuous deletion occurs (i.e., there is a deletion 5' to the cyclin box domain and 3' to the cyclin box domain). "Deletion" as used herein refers to both continuous and non-continuous deletions.

Fragments of the nucleic acid molecule-encoding a truncated human cyclin E protein, the truncated human cyclin E protein being a constitutively active form of human cyclin E protein, are best defined in the context of the deletion that occurs in the sequence of the wild-type cyclin E. The fragment consists essentially of a nucleotide sequence located 5' to the deletion, adjacent to a nucleotide sequence located 3' to the deletion (i.e. the fragment consists essentially of the nucleotide sequences flanking the deletion site). By "consists essentially of", it should be readily apparent that the essential part of the fragment is the nucleotide sequence that is at least 90% homologous to wild-type human cyclin E. Non-essential nucleotides could be placed at the 5' and/or 3' end of the fragment without affecting the binding properties of the essential nucleotide sequence. The term "adjacent" refers to the nucleotide sequence located 5' to the deletion site now being directly adjacent (next to; in continuous reading frame with) to the nucleotide sequence located 3' to the deletion site. Each of the deletion flanking sequences remains in its general original 5' to 3' order.

A fragment refers to a continuous portion of the truncated molecule that is less than the entire molecule. Preferably, the fragment consists of about 10 to about 30 nucleotides. The fragment is used to create an antisense nucleic acid molecule, and the standard length for such an antisense molecule is about 10 to about 30 nucleotides, and preferably 20 to 30 nucleotides. The fragment may be formed by taking 5 to 15 nucleotides from each of the deletion flanking regions. The fragment can also be used to detect the truncated protein forms, or to raise antibodies to detect the truncated protein forms. If the fragment is too long and has significant homology to wild-type cyclin E, the fragment and/or antibody will not distinguish between the wild-type and truncated forms.

The nucleic acid molecule encoding a truncated human cyclin E protein or antisense thereto can be inserted into a suitable host cell. Various methods for transforming host cells are known in the art. One of the first methods was microinjection, in which DNA was injected directly into the nucleus of cells through fine glass needles. This was an efficient process on a per cell basis, that is, a large fraction of the injected cells actually got the DNA, but only a few hundred cells could be injected in a single experiment.

The earliest method for introducing DNA into cells en masse was to incubate the DNA with an inert carbohydrate polymer (dextran) to which a positively charged chemical group (DEAE, for diethylaminoethyl) had been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell.

The DEAE-dextran method, while relatively simple, was very inefficient for many types of cells, so it was not a reliable method for the routine assay of the biological activity of a purified DNA preparation. The breakthrough that eventually made gene transfer a routine tool for workers studying mammalian cells was the discovery that cells efficiently took in DNA in the form of a precipitate with calcium phosphate. With this new method, the yield of virus from cells transfected with viral DNA was a hundred times greater than with the DEAE-dextran method.

Although calcium phosphate coprecipitation is the most widely used method for introducing DNA into mammalian cells, in some cells it doesn't work. Cells such as lymphocytes, which grow in suspension, are especially resistant to transfection by calcium phosphate precipitates.

In another method, electroporation, cells are placed in a solution containing DNA and subjected to a brief electrical pulse that causes holes to open transiently in their membranes. DNA enters through the holes directly into the cytoplasm, bypassing the endocytotic vesicles through which they pass in-the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. Microinjection, the surest way to get DNA into cells, can now be performed with a computer-assisted apparatus that increases by 10-fold or more the number of cells that can be injected in one experiment. And in an even more direct approach, used primarily with plant cells and tissues, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino et al. (1988), Shigekawa et al. (1988), Capecchi (1980), and Klein et al. (1987).

Since antisense RNA is very small and has a low molecular weight, the antisense RNA can be placed directly on mammalian cells in culture and the antisense RNA will be taken into the cells by diffusion.

Although naked DNA introduced by transfection can be transiently expressed in up to half the cells in a culture, more frequently the fraction of transiently transfected cells is much lower. In fact, some cells are almost completely refractory to transfection by the artificial methods described above. Many applications of recombinant DNA technology require introducing foreign genes into recalcitrant cell types. Potential gene therapy strategies, for example, require efficient means for transferring genes into normal human cells.

To solve this problem, researches have turned to viruses. Viral growth depends on the ability to get the viral genome into cells, and viruses have devised clever and efficient methods for doing it. The earliest viral expression vectors, based on the monkey tumor virus SV40, simply substituted some of the viral genes with the foreign gene. These recombinant molecules, prepared as bacterial plasmids, were transfected into monkey cells together with a second plasmid that supplied the missing viral genes. Once inside the cells, viral gene products produced from the two plasmids cooperate to replicate both plasmids and package each into virus particles. The virus stock that emerges from the cell is a mixture of two viruses, each of which is by itself defective (that is, it cannot replicate on its own because it is missing necessary viral genes). Nevertheless, this virus stock can then be used to infect new cells, efficiently introducing and expressing the foreign gene in the recipient cells.

A hybrid method that uses transfection to get DNA into cells and a viral protein to replicate it once inside is now commonly used for high-level production of protein from a cloned gene. This procedure uses a cell line, COS cells, carrying a stably integrated portion of the SV40 genome. These cells produce the viral T antigen protein, which triggers replication of viral DNA by binding to a DNA sequence termed the origin of replication. The foreign gene to be expressed is cloned into a plasmid that carries the SV40 origin of replication. After transfection into COS cells, the plasmid is replicated to a very high number of copies, increasing the expression level of the foreign gene.

Use of SV-40-based viral vectors is limited for a number of reasons: they infect only monkey cells, the size of foreign gene that can be inserted is small, and the genomes are often rearranged or deleted. Other viral vectors are more commonly used now, either because they can infect a wider range of cells or because they accept a wider range of foreign genes. Vaccinia virus is a large DNA-containing virus that replicates entirely in the cytoplasm. Early vaccinia vectors incorporated the foreign gene directly into a nonessential region of the viral genome. Recombinant viruses are viable and upon infection transcribe the foreign gene from a nearby viral promoter. Because the viral genome is large (185,000 bp), foreign genes cannot be inserted into vaccinia by standard recombinant DNA methods; instead, it must be done by recombination inside cells, a cumbersome and lengthy procedure. A more versatile vaccinia expression system uses a ready-made recombinant virus that expresses a bacteriophage RNA polymerase. The gene to be expressed is simply cloned into a plasmid carrying a bacteriophage promoter. The plasmid is transfected into cells that have been previously infected with the vaccinia virus that expresses the RNA polymerase. The gene on the plasmid is efficiently transcribed by the bacteriophage polymerase, accounting for up to 30 percent of the RNA in the cell. An additional feature of vaccinia virus infection is that the virus shuts down host cell protein synthesis so that viral mRNA (and mRNA from the plasmid) are preferentially translated into protein.

Another virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller (1989).

All of the viruses discussed above are lytic viruses, in that they enter cells, take over, replicate massively, and get out, killing the cell in the process. So these vectors cannot be used to introduce a gene into cells in a stable fashion. This task is most ably performed by retroviruses. Retroviruses are RNA viruses with a life cycle quite different from that of the lytic viruses. When they infect cells, their RNA genomes are converted to a DNA form (by the viral enzyme reverse transcriptase). The viral DNA is efficiently integrated into the host genome, where it permanently resides, replicating along with host DNA at each cell division. This integrated provirus steadily produces viral RNA from a strong promoter located at the end of the genome (in a sequence called the long terminal repeat or LTR). This viral RNA serves both as mRNA for the production of viral proteins and as genomic RNA for new viruses. Viruses are assembled in the cytoplasm and bud from the cell membrane, usually with little effect on the cell's health. Thus, the retrovirus genome becomes a permanent part of the host cell genome, and any foreign gene placed in a retrovirus ought to be expressed in the cells indefinitely.

Retroviruses are therefore attractive vectors because they can permanently express a foreign gene in cells. Moreover, they can infect virtually every type of mammalian cell, making them exceptionally versatile. Because of their versatility, retroviruses are also the vector of choice for gene therapy. In the design and use of retroviral vectors, the vectors usually contain a selectable marker as well as the foreign gene to be expressed. Most of the viral structural genes are gone, so these vectors cannot replicate as viruses on their own. To prepare virus stocks, cloned proviral DNA is transfected into a packaging cell. These cells usually contain an integrated provirus with all its genes intact, but lacking the sequence recognized by the packaging apparatus. Thus, the packaging provirus produces all the proteins required for packaging of viral RNA into infectious virus particles but it cannot package its own RNA. Instead, RNA transcribed from the transfected vector is packaged into infectious virus particles and released from the cell. The resulting virus stock is termed helper-free because it lacks wild-type replication-competent virus. This virus stock can be used to infect a target cell culture. The recombinant genome is efficiently introduced, reverse-transcribed into DNA (by reverse transcriptase deposited in the virus by the packaging cells), and integrated into the genome. Thus, the cells now express the new virally introduced gene, but they never produce any virus, because the recombinant virus genome lacks the necessary viral genes. For a review of retrovirus vectors, see Cepko (1988) and Eglitis et al. (1988).

Another viral vector is adenovirus, reviewed by Berkner (1988). Still another viral vector is herpesvirus.

The nucleic acid molecule encoding the truncated human cyclin E protein or antisense thereto can thus be inserted directly into a-host cell or into an intermediate expression vector. As indicated above, various expression vectors are known in the art, including plasmids, viral vectors, and bacteriophage vectors. The host cell to be transformed with the nucleic acid molecule may be most amenable to transformation with a particular type of expression vector. Plasmid vectors readily transform bacterial host cells. Viral vectors readily transform many mammalian cells. Baculovirus readily transforms insect cells.

The nucleic acid molecule is inserted into the expression vector using standard cloning procedures readily known in the art. This generally involves the use of restriction enzymes and DNA ligases, as described by Maniatis et al. (1982). U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/- or KS +/- (see "Stratagene Cloning Systems" Catalog (1993)), pQE, pIH821, pGEX, pET series (see Studier et al. (1990)), and any derivatives thereof.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria (e.g., *Agrobacterium tumefaciens*). The expression elements of these vectors vary in their strength and specificities. Depending upon the host-vector system utilized, any one of a number of suitable transcription and translation elements can be used.

Once the isolated nucleic acid molecule encoding the truncated cyclin E protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, and the like.

Biological markers can be used to identify the cells carrying recombinant DNA molecules. In bacteria, these are commonly drug-resistance genes. Drug resistance is used to select bacteria that have taken up cloned DNA from the much larger population of bacteria that have not. In the early mammalian gene transfer experiments involving viral genes, the transfer of exogenous DNA into cells was detected because the DNA had a biological activity, it led to production of infectious virus or produced stable changes in the growth properties of the transfected cells. It was then discovered that the DNA tumor virus, herpes simplex virus (HSV), contained a gene encoding the enzyme thymidine kinase (the tk gene). The HSV tk gene can be used as a selectable genetic marker in mammalian cells in much the same way that drug-resistance genes worked in bacteria, to allow rare transfected cells to grow up out of a much larger population that did not take up any DNA. The cells are transferred to selective growth medium, which permits growth only of cells that took up a functional tk gene (and the transferred DNA of interest). Various dominant selectable markers are now known in the art, including:

aminoglycoside phosphotransferase (APH), using the drug G418 for selection which inhibits protein synthesis; the APH inactivates G418;

dihydrofolate reductase (DHFR): Mtx-resistant variant, using the drug methotrexate (Mtx) for selection which inhibits DHFR; the variant DHFR is resistant to Mtx;

hygromycin-B-phosphotransferase (HPH), using the drug hygromycin-B which inhibits protein synthesis; the HPH inactivates hygromycin B;

thymidine kinase (TK), using the drug aminopterin which inhibits de novo purine and thymidylate synthesis; the TK synthesizes thymidylate;

xanthine-guanine phosphoribosyltransferase (XGPRT) using the drug mycophenolic acid which inhibits de novo GMP synthesis; XGPRT synthesizes GMP from xanthine; and adenosine deaminase (ADA), using the drug 9$\beta$-D-xylofuranosyl adenine (Xyl-A) which damages DNA; the ADA inactivates Xyl-A.

Gene amplification can also be used to obtain very high levels of expression of transfected gene. When cell cultures are treated with Mtx, an inhibitor of a critical metabolic enzyme, DHFR, most cells die, but eventually some Mtx-resistant cells grow up. A gene to be expressed in cells is cotransfected with a cloned dhfr gene, and the transfected cells are subjected to selection with a low concentration of Mtx. Resistant cells that have taken up the dhfr gene (and, in most cases, the cotransfected gene) multiply. Increasing the concentration of Mtx in the growth medium in small steps generates populations of cells that have progressively amplified the dhfr gene, together with linked DNA. Although this process takes several months, the resulting cell cultures capable of growing in the highest Mtx concentrations will have stably amplified the DNA encompassing the dhfr gene a hundredfold or more, leading to significant elevation of the expression of the cotransfected gene.

Once the nucleic acid molecule encoding the truncated cyclin E has been inserted into a host cell, with or without the use of an intermediate expression vector, the host cell can be used to produce the truncated cyclin E protein by culturing the cell under conditions suitable for translation of the DNA molecule, thereby expressing the truncated human cyclin E protein. The truncated human cyclin E protein can then be recovered from the cell. Generally, the truncated human cyclin E protein of the present invention is produced in purified form by conventional techniques, such as by secretion into the growth medium of recombinant *E. coli*. To isolate the truncated protein, the *E. coli* host cell carrying a recombinant plasmid is propagated, homogenized, and the homogenate is centrifuged to remove bacterial debris. The supernatant is then subjected to sequential ammonium sulfate precipitation. The fraction containing the truncated protein of the present invention is subjected to gel filtration in an appropriately sized dextran or polyacrylamide column to separate the proteins. If necessary, the protein fraction may be further purified by HPLC.

Full length cDNA clones for the truncated human cyclin E proteins can be inserted into appropriate expression vectors and used in gene transfer experiments to set up transient and stable expression systems in mammalian cell lines.

a) Transient Expression Systems

A transient expression system [Gorman (1985)], can be used due to the rapidity possible with this assay. Messenger RNA and protein synthesis can be analyzed within 48 hours after the introduction of DNA. Large quantities of specific mRNA (as much as 1% of total cellular mRNA) frequently can be expressed. In contrast, construction of stable transformed cell lines is lengthy, and the levels of expression of mRNA are frequently below that obtained with transient systems. Several questions are most efficiently addressed in these systems: 1) which cell types and vectors are most efficient in expressing transfected truncated cyclin E cDNAs; and 2) which cell types are capable of expressing truncated cyclin E proteins which retain their native functional properties.

Truncated cyclin E cDNA can be introduced into SV40 expression vectors (e.g., pSV2) into COS-7 cells, using the calcium phosphate [Wigler, M., et al. (1978)] or DEAE-Dextran [Lopata, M. A., et al. (1984)] transfection procedures. Previous studies with transfection of nAcetyl choline receptor (nAChR) genes found significant transcription of AChR mRNA to levels of about 1% of total mRNA in transfected cells. Claudio, T., et al. (1987); Claudio, T., et al. (1984). Transfected cells can be tested for their level of expression of truncated cyclin E mRNA species. Other common cell types can also be tested for transient transfection, e.g., CHO cells, mouse fibroblasts (L cells, 3T3 or 3T6 cells), HeLa cells, neuroblastoma, L6 muscle cells, etc. Studies with primate cells utilize SV40 expression vectors, whereas studies with other cells utilize Rous Sarcoma Virus vectors (i.e., PRSV), which is the most ubiquitous promotor for efficient transient expression.

b) Stable Expression Systems

Stable cell lines [Claudio et al., (1987); Claudio et al. (1984)] with transfected truncated cyclin E cDNAs can be established for detailed pharmacological and biochemical characterization. Transient expression experiments can be used to determine which viral expression vectors are most efficient in particular cell types. For instance [Gorman (1985)], cells can be co-transfected with truncated cyclin E cDNA in a pSV or pRSV vector, along with a dominant selectable marker such as gpt or neoR (i.e., in vectors prSV-gpt or pRSV-neo). The cells will be subcultured into a selective medium two days following transfection, and then once every 4–5 days thereafter until discrete colonies can be seen on transfected plates, requiring 1–2 months to establish stable cell lines. Cells selected by dominant marker can then be tested for expression of truncated cyclin E as well.

A transformed cell containing the truncated cyclin E protein can also be utilized for gene therapy purposes. Note that the cell may be transformed in vitro and reinserted into a multicellular organism, or the cell may be transformed in vivo. In the same way that a retrovirus acts as a vector to carry a gene into a cell, so the cell can be regarded as a vector for carrying the gene into a patient's body.

Suitable cells for transformation and use in gene therapy should be readily obtainable, grow well in culture, and be able to withstand the various manipulations involved in, for example, retrovirus infection. For in vitro transformation, vector cells should be easy to return to the patient after such transformation and should continue to live for many months, preferably for the life of the patient. See Friedmann (1989), Verma (1990), Anderson (1992), and Mulligan (1993) for discussions of gene therapy.

Drugs, such as peptide drugs, can be made using various methods known in the art. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley and Smith 1988). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley and Smith 1988; Cwirla et al. 1990; Scott and Smith 1990; Christian et al. 1992; Smith and Scott 1993).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley and Smith 1988; Scott 1992).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found. LaRocca et al. (1992) expressed a mimotope of the human breast epithelial mucin tandem repeat in *Escherichia coli*. Balass et al. (1993) identified a hexapeptide that mimics a conformation-dependent binding site of the acetylcholine receptor. Hobart et al. (1993) isolated a mimotope that mimics the C6 epitope (the epitope for the sixth component of complement).

The sequences of these mimotopes, by definition, do not identify a continuous linear native sequence or necessarily occur in any way in a naturally-occurring molecule, i.e. a naturally occuring protein. The sequences of the mimotopes merely form a peptide which functionally mimics a binding site on a naturally-occurring protein. For example, the mimotope of Balass et al. (1993) mimics the binding site of the acetylcholine receptor.

Many of these mimotopes are short peptides. The availability of short peptides which can be readily synthesized in large amounts and which can mimic naturally-occurring sequences (i.e. binding sites) offers great potential application.

Using this technique, mimotopes to a monoclonal antibody that recognizes a truncated human cyclin E protein form, or fragments thereof, or that recognize the antisense sequences or fragments thereof, can be identified. The sequences of these mimotopes represent short peptides which can then be used in various ways, for example as peptide drugs. Once the sequence of the mimotope is determined, the peptide drugs can be chemically synthesized.

The truncated proteins or fragments thereof, and the drugs, such as peptide drugs, disclosed herein, may be administered alone or in combination with compatible carriers as a composition. Compatible carriers include suitable pharmaceutical carriers or diluents. The diluent or carrier ingredients should be selected so that they do not diminish the therapeutic effects of the proteins, fragments, or drugs of the present invention.

The compositions herein may be made up in any suitable form appropriate for the desired use; e.g., oral, parenteral, or topical administration. Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

Additional lower molecular weight truncated forms of cyclin E can be identified by several techniques, including: a) Direct Edman sequencing of the lower molecular weight aberrant expressed cyclin E isoforms; b) Mass spectrometry for the characterization/identification of cyclin E isoforms isolated by 2-D PAGE; and c) Anti-peptide antibody identification of cyclin E isoforms.

The lower molecular weight isoforms of cyclin E from breast cancer cells can be directly sequenced. Lower molecular weight isoforms of cyclin E which have been electroeluted to a PVDF membrane will be subjected to automated Edman analysis to determine amino terminal sequences. Since about 70% of all proteins have a blocked N-terminal amino acid, it is very possible that cyclin E is also blocked. For that purpose, Immobolin CD bound protein will also be reduced and alkylated in situ and cleaved with CNBr to generate internal fragments. The resultant fragments will be solubilized, separated by SDS-PAGE, stained, and blotted; excised bands will then be subjected to automated Edman analysis. The sensitivity of Edman sequencing is in the range of 50–500 pmoles, and as such cyclin E 2-D spots blotted to the membrane may not provide enough extracted protein to allow for such direct analysis of these lower molecular weight isoforms. In that case, mass spectrometry analysis of these cyclin E isoforms can be performed.

Many studies have recently been published that describe the application of mass spectrometry for the characterization/identification of proteins isolated by 2-D PAGE (Hall et al. 1993; Henzel et al. 1993; and Rasmussen et al. 1994). The typical strategy is electroelution of protein spots onto a PVDF membrane (e.g. Immobolin P, ProBlott, etc.) followed by Ponceau S or amido black staining. A specific spot is then excised from the membrane, destained, diced, and placed in a 500 $\mu$l Eppendorf tube. The bound protein is reduced and alkylated, and the membrane is then treated with PVP 40 or RTX-100. Digestion is accomplished with the addition of proteolytic enzyme (trypsin, endo glu-C, etc.) in a Tris buffer solution. Membrane and solution are sonicated and then spun, with the supernatant collected for microbore/capillary reverse phase HPLC (RP HPLC).

Direct RP HPLC ESI-MS (electrospray ionization) with microcapillary columns (100 $\mu$M ID) for digest molecular weight mapping is readily accomplished at the femtomole level. Peptide sequence information from HPLC ESI-MS/MS is also possible at this sample level, with the caveat that not all peptides are determinant at this level. Alternatively, femtomole amounts of fractionated peptides can be analyzed for molecular weight by MALDI TOF MS using a polycrystalline matrix preparation technique or polyethylene membranes, although some peptides may be lost with these methods (Blackledge 1995).

Recombinant cyclin E will be used initially as a model for the optimization of proteolytic enzyme cleavage, sample handling, and mass spectrometry conditions. Truncated cyclin E isolated by 2-D PAGE will then be treated with the developed protocol. Also, truncated cyclin E will be electroeluted from the 2-D gel into a polyethylene film and analyzed by MALDI TOF MS for the weight of the intact protein. As the complete gene sequence of cyclin E is known, molecular weight information from a proteolytic digest will indicate the nature of the truncated structures. For example, a set of expected tryptic peptide cleavage products can be readily calculated from the gene sequence for a protein that results from a DNA frame shift or a small number of splice variants. Common protein modifications, such as phosphorylation or ribosylation, of the normal protein or a frame shift variant (i.e. $\Delta$148) are also recognizable from a tryptic digest LC ESI-MS or MALDI TOF MS molecular weight map alone. Digestion with other proteases, such as endo Glu-C, etc., can also be done. Sequence information to demonstrate the primary structure/modifications of the truncated cyclin E will be obtained by ESI-MS/MS or MALDI TOF post source decay (PSD) analysis. A Bruker Reflex MALDI TOF has the capability to pre select a specific peptide ion from a digest mixture for PSD analysis. This is a new method that allows sequence information from femtomole mixtures of peptides.

Anti-peptide antibody identification is an alternative, less direct, approach for the identification of the lower molecular weight isoforms of cyclin E. This is accomplished by developing antibodies to peptides that are strategically situated along the protein. The molecular weight range of cyclin E and its lower molecular weight isoforms are between 35–50 KDa, and the entire sequence for cyclin E is known and published (SEQ ID NO:1, Koff et al.). Ten different peptides will be chosen, 30 amino acids each (i.e. 5 KDa), that are separated from each other by 2 amino acids along the entire cyclin E protein sequence. These peptides will be conjugated to Ovalbumin, and used for the development of polyclonal antibodies. These antibodies can be used on Western blot analysis to detect the lower molecular weight isoforms. This will provide information as to the partial identity of each isoform. One antibody may react with several of the isoforms, or hybridization may occur only with one isoform. Based on the molecular weight of the isoform and position of the anti-peptide antibody along the cyclin E sequence, information can be obtained about the identity of the isoforms. These additional isoforms can be targeted therapeutically.

Materials and Methods

Cells lines, Culture Conditions, and Tissue Samples.

The culture conditions for 70N, 81N, and 76N normal cell strains and MCF-7, MDA-MB-157, MDA-MB-231, MDA-MB-436, T47D, BT-20, HBL100, Hs578T, SKBR3, and ZR75 T tumor cell lines were described previously (Keyomarsi & Pardee, 1993). MCF-10A is a normal human mammary epithelial cell line which is spontaneously immortalized and does not grow in soft agar and is not tumorigenic in nude mice (Soule, et al., 1990). This cell line was obtained from ATCC and is cultured in DFCI-1 (Band & Sager, 1989). All cells were cultured and treated at 37° C. in a humidified incubator containing 6.5% $CO_2$ and maintained free of Mycoplasma as determined by the MycoTect Kit (GIBCO). Snap frozen surgical specimens from patients diagnosed with breast cancer were obtained from the National Disease Research Interchange/Cooperative Human Tissue Network, Eastern Division. The clinical stage and grade of the tissue samples used were obtained from pathology/surgical reports.

Synchronization and Flow Cytometry.

76N normal mammary epithelial cell strain and MDA-MB-157 tumor cell line were synchronized at the G1/S boundary by a modification of the double thymidine block procedure (Rao et al., 1970.). Briefly, 48 h after the initial plating of cells, the medium was replaced with fresh medium containing 2 mM thymidine for either 24 h (76N cells) or for 36 h (MDA-MB-157 cells). This medium was then removed, the cells were washed three times, and subsequently incubated in fresh medium lacking thymidine for 12 h (76N cells) or 24 h (MDA-MB-157 cells). Next cells were re-incubated in medium containing 2 mM thymidine, as above, washed with fresh medium, and incubated in thymidine free medium for the rest of the experiment. Cells were harvested at the indicated times, cell density was measured electronically using a Coulter Counter (Hialeah, Fla.) and flow cytometry analysis was performed. For flow cytometry studies, $10^6$ cells were centrifuged at 1000×g for 5 min, fixed with ice-cold 70% ethanol (30 min at 4° C.), and washed with phosphate buffered saline (Crissman et al., 1974). Cells were suspended in 5 ml of phosphate-buffered saline containing 10 $\mu$g/ml RNase, incubated at 370° C. for 30 min, washed once with phosphate buffered saline, and resuspended in 1 ml of 69 $\mu$M propidium iodide in 38 mM sodium citrate. Cells were then incubated at room temperature in the dark for 30 min. and filtration through a 75 mm Nitex mesh. DNA content was measured on a FACScan flow cytometer system (Becton Dickinson, San Jose, Calif.), and data were analyzed using CELLFIT software system (Becton Dickinson).

Western Blot and H1 Kinase Analysis.

Cell lysates and tissue homogenates were prepared and subjected to Western blot analysis as previously described (Keyomarsi, et al., 1994; Keyomarsi & Pardee, 1993). Briefly, 100 $\mu$g of protein from each tissue sample or cell line (for sf9 extracts, 50 $\mu$g) were electrophoresed in each lane of a 10% sodium dodecyl sulfate-polyacrylamide gel (SDS-PAGE) (cyclin E and cyclin A), or a 13% SDS-PAGE (cdk2 and all Sf9 cell extracts) and transferred to Immobilon P. Blots were blocked with 20 mM Tris-HCl, pH 7.5, 150 mM NaCl, 5% dried milk, 0.2% Tween overnight at 4° C. and were incubated with various primary antibodies diluted in blocking buffer for 3 hours. Primary antibodies used were rabbit anti-human cyclin E serum at a dilution of 1:2500, monoclonal antibody HE12 to cyclin E at a dilution of 1:10, affinity-purified rabbit anti-human p33$^{cdk2}$ kinase antibody at a dilution of 1:2000, and affinity-purified rabbit anti-human cyclin A antibody at a dilution of 1:20,000. Following primary antibody incubation, the blots were washed and incubated with either goat anti-mouse or anti-rabbit horseradish peroxidase conjugate at a dilution of 1:5000 in blocking buffer for 1 h, and finally washed and developed with detection reagents (ECL) supplied by Amersham Biochemicals. ECL exposures for all Western blots are of similar duration, i.e. 1–10s.

For H1 kinase assays, 250 $\mu$g of protein (unless otherwise indicated) were used for immunoprecipitation with either polyclonal antibody to cyclin E or CDK2 in lysis buffer containing 50 mM Tris HCl pH 7.5, 250 mM NaCl, 0.1% NP-40, 25 $\mu$g/ml leupeptin, 25 $\mu$g/ml aprotinin, 10 $\mu$g/ml pepstatin, 1 mM benzamidine, 10 $\mu$g/ml soybean trypsin inhibitor, 0.5 mM PMSF, 50 mM NaF, 0.5 mM Sodium Ortho-Vanadate. The protein/antibody mixture was incubated with protein A Sepharose for 1 hour and the immunoprecipitates were then washed twice with lysis buffer and four times with kinase buffer (50 mM Tris HCl pH 7.5, 250 mM NaCl, 10 mM $MgCl_2$, 1 mM DTT, and 0.1 mg/ml BSA). Immunoprecipitates were then incubated with kinase buffer containing 5 $\mu$g histone H1, 60 $\mu$M cold ATP, and 5 $\mu$Ci of [$^{32}$p] gATP in a final volume of 50 $\mu$l at 37° C. for 30 min. The products of the reaction were then analyzed on a 13% SDS-PAGE gel. The gel was then stained, destained, dried and exposed to X-ray film. For quantitation, the protein bands corresponding to histone H1 were excised and radioactivity was measured by scintillation counting.

Reverse Transcription-Polymerase Chain Reaction Amplification (RT-PCR).

RNA was isolated from cell lines and tissue samples as previously described (Keyomarsi & Pardee, 1993). To remove chromosomal DNA contamination from RNA, 50 $\mu$g of total cellular RNA was incubated for 30 min at 37° C. with 10 units of RNasin (Promega) and 20 units of RQI DNase (Promega) in 10 mM Tris HCl, pH 8.3, 50 mM KCl, 1.5 mM $MgCl_2$. After extraction with phenol/$CHCl_3$ (1:1) followed by $CHCl_3$, the supernatant was ethanol precipitated in the presence of 0.3 M NaOAC and RNA was redissolved in 0.1 X Tris-EDTA in diethyl pyrocarbonate-treated water. Reverse transcription was performed by incubating 1 $\mu$g of the DNase treated RNA with 300 units of Moloney Murine Leukemia Virus reverse transcriptase (MMLV RT) (GIBCO/BRL) in the presence of 15 $\mu$M oligo-dT$_{(12-18)}$ (Pharmacia) as a primer and 20 $\mu$M DNTP for 10 min at room temperature, 45 min at 42° C., 5 min at 99° C. and 5 min at 5° C. in the Gene Amp PCR system 9600 (Perkin Elmer Cetus, San Diego, Calif.). One half of the reaction was subsequently used for 30 cycles of PCR amplification using GeneAmp PCR reagent kit (Perkin Elmer Cetus). PCR cycles include denaturation for 40 seconds at 94° C., annealing for 1 min at 61° C., and polymerization for 1 min at 72° C. A minimum of 3 independent PCR amplifications from each specimen, for each experiment, were performed to guard against potential errors due to Taq polymerase misincorporation.

Oligonucleotides, Cloning and Sequencing of RT-PCR Products.

A pair of primers L1CYCE: 5'-GGGATGCGAAGGAGCGGGACA-3' (SEQ ID NO:5) and R1CYCE: 5'-AGCGGCGCAACTGTCTTTGGT-3' (SEQ ID NO:6) based on the mRNA sequence of cyclin E (Koff, et al., 1991; Lew, et al., 1991) were designed to amplify the entire cyclin E coding sequence of human cyclin E cDNA. To specifically amplify the cyclin E transcripts harboring the Δ9 and Δ148 deletion, the following sets of primers were used respectively: LMEMARK3:

5'-GCAAACGTGACCGTTG-3' (SEQ ID NO:7) and R1CYCE: 5'-AGCGGCGCAACTGTCTTTGGT-3' (SEQ ID NO:6); L1CYCE: 5'-GGGATGCGAAGGAGCGGGACA-3' (SEQ ID NO:5) and RMEMARK3: 5'-ACCGCTCTGTGCTTCATC-3' (SEQ ID NO:8). The PCR products were visualized by fractionating ⅕th of each reaction on a 1.5% agarose gel stained with ethidium bromide. A fraction of each reaction was then used to clone the RT-PCR products into the PCR II vector using the TA cloning system from Invitrogen (San Diego, Calif.). Plasmid DNA sequencing of cloned cDNA products with either T7 of SP6 primer was carried out using Sequenase 2.0 sequencing kit from United States Biochemicals Co. (Cleveland, Ohio). Fifteen clones from each independent RT-PCR reaction (at least 3) were completely sequenced in both orientations to confirm the sequences for Δ9 and Δ148 variants of cyclin E.

In Vitro Translation.

To transcribe and translate the cyclin E cDNAs cloned in the PCR II vector, the TNT coupled Reticulocyte Lysate system (Promega) was used. Briefly, 1 μg of PCR II vector containing either cyclin E-wt, cyclin E-Δ9, or cyclin E-Δ148 was added to rabbit reticulocyte lysate (50% of total volume) in the presence of T7 RNA polymerase, 1 mM amino acid mixture minus methionine, 40 μCi $^{35}$S-methionine (Dupont), RNasin ribonuclease inhibitor and the TNT reaction buffer (Promega) in a total volume of 50 μl. For non-radioactive reactions, unlabeled methionine was added to the mix and radioactivity was excluded. The reactions were then incubated at 30° C. for 2 hours and the translated radioactive products were separated by SDS-PAGE. The gels were then stained, destained, fluorographed, dried and the protein products were visualized by autoradiography. For visualization of the non-radioactive samples, the translation products were subjected to Western blot analysis using a polyclonal antibody specific to cyclin E.

Production of Cyclins and Kinases in Insect Cells.

The cDNAs of cyclin E wild-type, cyclin E-Δ9, cyclin E-Δ148, and cdk2 were subcloned into pMP3 (Pharmingen) plasmid containing the Basic Protein promoter that is active during and after viral DNA synthesis when the cell is producing baculovirus components to assemble the virus particles. At this stage there are larger numbers of modifying enzymes present which will increase the effectiveness of post-translational modification of the gene product of interest. Once the plasmids were constructed, they were individually co-transfected in sf9 insect cells with the linearized BaculoGold (Pharmingen) virus DNA (containing a lethal deletion), which through recombination would only produce viable recombinant baculovirus expressing the clones. The titer of all the supernatants were determined and insect cells were then infected with a plaque-forming unit/cell number of 1.

EXAMPLE 1

Elevated Cyclin E Associated Kinase Activity in Breast Cancer Cells.

To test the hypothesis that the altered expression pattern of cyclin E protein found in tumor cell lines and tissue samples (Keyomarsi, et al., 1994) is associated with increased cyclin E kinase activity, cyclin E expression and activity in two normal versus five human breast cancer cell lines was compared. The two normal cell lines are the normal human mortal breast epithelial cell strain, 76N, obtained from reduction mammoplasty, and a normal immortalized human breast epithelial cell line, MCF-10A (Soule et al., 1990). 76N is a mortal cell strain since it rapidly proliferates (doubling time of 24–27 hrs) for multiple passages before senescence at around passage 20 (Band et al., 1989). The MCF-10A cell line is a spontaneously immortalized human breast epithelial cell line which can be cultured indefinitely. This cell line has no tumorigenicity potential but retains characteristics of a normal breast epithelial cell line (Soule, et al., 1990). The five human breast cancer cell lines used were MDA-MB-157, MDA-MB-436, ZR75T, SKBR3, and MCF-7.

The pattern of cyclin E protein expression was examined in normal versus tumor cell lines using monoclonal and polyclonal antibodies to cyclin E on Western blots. Whole cell lysates were extracted from the seven cell lines (100 μg of protein extract/lane), run on a 10% acrylamide gel and blotted as described in Materials and Methods. Similar immunoblot banding patterns were obtained with either the monoclonal or polyclonal antibody to cyclin E, confirming the specificity of the multiple bands. However, the patterns of cyclin E protein expression was different between normal and tumor cells. Both cyclin E antibodies recognized one major protein migrating at ~50 KDa, and two much less abundant lower molecular weight forms (~43 KDa and ~35 KDa), in the two normal cell lysates. In the tumor cell lysates on the other hand, the same antibodies recognized three (~50 KDa, ~43 KDa, and ~35 KDa), two (~50 KDa and ~43 KDa, or ~43 KDa and ~35 KDa) or one (~35 KDa) additional and highly abundant isoforms of cyclin E protein that in each case revealed a different pattern from that of the normal cells.

The cyclin E associated protein kinase activity in all cells was then analyzed by measuring the phosphorylation of histone Hl in immunoprecipitates made with the polyclonal antibody to cyclin E. In all of the tumor cell lysate immunoprecipitates, the activity levels of cyclin E-associated kinase were significantly higher than that of both normal cells. For example, in MDA-MB-436 and SKBR3 tumor cell lines which express only the lower molecular weight isoforms of cyclin E protein, the associated kinase activity was six fold greater-than that of the normal cells which express mainly the high molecular weight, 50 KDa, form of cyclin E protein. Similarly, the other tumor lines containing altered patterns of cyclin E expression, had significantly higher cyclin E-associated H1-kinase activity as compared to the normal cell strains.

EXAMPLE 2

Lack of Cell Cycle Regulation of Cyclin E in Breast Cancer Cells.

In one tumor line, MDA-MB-157, the level as well as the associated kinase activity of cyclin E protein was the highest of all the tumor cell lines examined. Previous studies (Keyomarsi & Pardee, 1993) showed that this overexpression is in part due to an 8-fold amplification of the cyclin E gene and 64 fold overexpression of its mRNA in this cell line. The cyclin E gene is amplified in tandem and is not associated with gross genomic rearrangements. To investigate whether the signals required for normal regulation of cyclin E expression are altered or lost in tumor cells, the cell cycle expression of cyclin E protein and its associated kinase activities in the MDA-MB-157 tumor cell line were compared to normal mammary epithelial 76N cells.

Both cell lines were synchronized in the G1/S border by double thymidine block (see Materials and Methods). Synchrony of both cell types at several times after release from the block was monitored by flow cytometry. The doubling times of the normal 76N and tumor MDA-MB-157 cells are 27 and 36 h, respectively, and their DNA content distribution in different cell cycle phases are as follows: 76N- G1(75%), S (4%), and G2/M (21%); MDA-MB-157- G1 (56%), S (13%), and G2/M (31%). At various times after release from treatment for synchronization, cells were harvested and extracted proteins were analyzed on Western blots with antibodies to cyclins E and A. Protein (50 μg) for each time point was applied to each lane of a 10% acrylamide gel and blotted. The same blot was reacted with cyclin E monoclonal (HE12) and cyclin A affinity purified polyclonal antibodies. The blots were stripped between the two assays in 100 mM β-mercaptoethanol, 62.5 mM Tris HCl (pH 6.8), and 2% SDS for 30 min at 55° C. In normal 76N cells, the pattern of expression of cyclin E and cyclin A proteins is consistent with that seen for other normal cell types with levels rising prior to S phase and oscillating thereafter in the cell cycle (Koff et al., 1992). In addition there is only one major form (i.e., 50 KDa) of cyclin E protein detected and there is a shift in the timing of when cyclin E versus cyclin A appears in the cell cycle of these normal epithelial cells. However, in the tumor cells, cyclin E protein does not appear to be cell cycle regulated and multiple isoforms of the protein are also present with similar signal intensities and banding patterns during the time intervals examined. In addition when these tumor cells are synchronized by other agents, such as Lovastatin (Keyomarsi et al., 1991), cyclin E expression is also constituitive throughout the cell cycle, resembling a pattern identical to that shown in tumor cells. In the same tumor cell extracts, cyclin A protein is cell cycle regulated with peak levels coinciding with peak S and early G2/M phase. Hence, it appears that in this tumor cell line, cyclin E is abnormally regulated during the cell cycle.

In order to compare the kinase activity associated with cyclin E and cdk2 in normal and tumor cells, the phosphorylation of histone H1 in immunoprecipitates prepared from synchronous cell extracts was measured using antibody to either cyclin E or cdk2. Equal amount of proteins (600 μg) from cell lysates prepared from each cell line were immunoprecipitated with anti-cyclin E (polyclonal) or anti-CDK2 (polyclonal) coupled to protein A beads using histone H1 as substrate. There were two significant differences found between normal and tumor cells: First, in the length of time which an active cyclin E/cdk2 complex is present, and secondly in the amount of kinase activity associated with cyclin E versus cdk2 during the normal and tumor cell cycles. In normal cells, both cyclin E associated kinase and cdk2 activities are cell cycle regulated, coinciding with the levels of cyclins E and A protein expression. In addition, the cdk2 activity is one order of magnitude (i.e 10 fold) higher than cyclin E associated activity, consistent with cdk2's ability to form an active complex with other cyclins besides cyclin E in normal cells. Hence, cyclin E in these normal cells is indeed cell cycle regulated and the signals required for such regulation are intact both at the protein expression level and kinase activity.

In tumor cells, on the other hand, cyclin E is not cell cycle regulated and remains in a catalytically active complex throughout the cell cycle resulting in a constitutive pattern of histone H1 phosphorylation. The basal levels of cyclin E associated kinase activity during the tumor cell cycle, at any time interval examined, are at least 20 times higher than that of the normal cells. Cdk2, a kinase which binds to both cyclin E and A, is also constitutively active during the cell cycle. However, cdk2 activity in this tumor cell line is only 2 fold higher than cyclin E associated kinase activity, presumably due to the abundance of cyclin E protein which is capable of sequestering cdk2. When cyclin A protein levels are induced in the tumor cells, there is only a 30% additional induction in cdk2 associated activity. These observations suggest that cyclin E protein, which is constitutively expressed in the cell cycle of tumor cells, also results in an active kinase complex throughout the cell cycle. Furthermore, since the same cyclin-dependent kinase can be regulated by both cyclins E and A, increased levels of cyclin E may overcompensate for cyclin A regulation, again resulting in a constitutively active and abundant cyclin E/cdk2 complex.

EXAMPLE 3
Isolation of Variant Forms of Cyclin E Transcripts.

In an attempt to determine the presence of any potential alterations in the cyclin E gene in MDA-MB-157, the entire cyclin E coding region of this cell line was amplified by reverse transcription-polymerase chain reaction amplification (RT-PCR). PCR conditions were carried out as described in Materials and Methods. PCR products were separated on a 1.5% agarose gel and stained with ethidium bromide. These products were cloned and their DNA sequences were analyzed. Using a pair of primers flanking the entire coding sequence of the cyclin E gene (primer L1CYCE having a nucleotide sequence as shown in SEQ ID NO:5 and primer R1CYCE having a nucleotide sequence as shown in SEQ ID NO:6), at least two distinct PCR products ranging in size from 1.0 to 1.2 kb from the MDA-MB-157 RT template were observed. The product from the control (cyclin E plasmid DNA) was of 1.2 kb, corresponding to the full length cyclin E cDNA isolated from a HeLa cDNA library (Koff et.al., 1991; Lew et al., 1991). The RT-PCR products from the MDA-MB-157 cell line were cloned and their identity was confirmed by Southern blotting and by DNA sequencing. Three independent RT-PCR reactions were performed on freshly isolated RNA from this cell line. Fifteen clones from each RT-PCR reaction were examined further. Sequence analyses revealed two types of truncated variants of the cyclin E gene, as well as an unequivocally normal sequence, from the MDA-MB-157 cell line.

The PCR products containing these two truncated variants were termed cyclin E-Δ9 and cyclin E-Δ148 (FIG. 1). The alteration in clone cyclin E-Δ9 is a 9 base pair in-frame deletion of nucleotides 67–75 (as shown in SEQ ID NO:2) at the 5' end of the gene, while the alteration in clone cyclin E-Δ148 is a 148 base,pair deletion of nucleotides 1000–1147 (as shown in SEQ ID NO:2) at the 3' end of the gene resulting in a frame shift transcript. Curiously, the 148 bp deletion in cyclin E Δ148 clone disrupts the PEST sequence motif of the gene, which is thought to be important for its role in degradation of the protein product (Koff et al., 1991; Lew et al., 1991). The relative positions of these two newly identified truncations to the wild type sequence of cyclin E are shown in FIG. 1. In vitro translation studies were performed on these clones. The cDNAs of cyclin E clones were subcloned into PCR II vector and transcribed and translated in vitro using T7 RNA polymerase-rabbit reticulocyte lysate system in the presence of $^{35}$S-methionine and products were analyzed on a 10% SDS-PAGE followed by autoradiography. Cyclin E-wt and cyclin E-Δ9 protein products showed very similar electrophoretic mobilities. Cyclin E-Δ148 gives rise to a protein product which is ~5 kd smaller than the cyclin E-wt, which would correspond to the loss of the 50 amino acids. To confirm that the protein products from in vitro translation reactions were indeed cyclin 2, the cDNAs of the three different clones were transcribed and translated in the presence of unlabeled methionine and the products were subjected to Western blot analysis. The protein products from cyclin-wt, Δ9 and Δ148 clones reacted strongly with the polyclonal antibody to cyclin E, suggesting that the in vitro translated products of these clones are truncated forms of cyclin E. Interestingly, all the clones gave rise to two major protein products, migrating at ~45 and ~38 kd for cyclin E-wt and Δ9 clones, and ~40 and ~33 kd for cyclin E-Δ148 clone.

EXAMPLE 4

Expression of Cyclin E Truncated Variants in Normal Versus Tumor Cells and Tissue Samples.

Since these two truncated forms of cyclin E cDNA were isolated from one tumor-derived cell line, the generality of expression of the cyclin E variants in a panel of 13 breast epithelial cell lines was examined. These cell lines included 3 normal mortal cell strains (70N, 81N, and 76N), 1 normal immortalized cell line (MCF-10A), and 9 tumor-derived breast cell lines (MCF-7, MDA-MB-157, MDA-MB-231, MDA-MB-436, T47D, BT-20T, HBL-100, Hs578T, and ZR75T). The RT-PCR amplification of cyclin E coding sequence from normal and tumor-derived breast epithelial cell lines used primers (L1CYCE and R1CYCE, having a nucleotide sequence as shown in SEQ ID NO:5 and SEQ ID NO:6, respectively) flanking the coding region of cyclin E and amplifying wild-type cyclin E sequences; as well as those containing internal deletions, primers (LMEMARK3 and R1CYCE, having a nucleotide sequence as shown in SEQ ID NO:7 and SEQ ID NO:6, respectively) spanning the Δ9 deletion and amplifying only those cyclin E sequences harboring the Δ9 internal deletion of cyclin E; and primers (L1CYCE and RMEMARK3, having a nucleotide sequence as shown in SEQ ID NO:5 and SEQ ID NO:8, respectively) spanning the Δ148 internal deletion and amplifying only those cyclin E sequences containing the Δ148 deletion. These analyses revealed the presence of multiple transcripts of cyclin E in all cell lines examined. However, no distinct differences were observed in their pattern of expression between normal versus tumor cell lines. Furthermore, sequence analysis of a cloned RT-PCR product of 76N normal cells revealed that the major transcript found in this normal cell strain is the Δ148 variant of cyclin E previously identified in MDA-MB-157 tumor cell line. These observations indicate that the Δ148 RNA is expressed in all cells examined at an apparently higher level than the wild-type species of cyclin E RNA. To examine the specific expression of Δ9 and Δ148 in each cell line, RT-PCR was performed using primers that spanned the deleted sequences, such that only those cell lines containing cyclin E transcripts harboring these deletions would give rise to products. These analyses show that the Δ69 variant form of cyclin E is abundantly present in 3 cell lines, two of which are normal cell strains and one is the MDA-MB-157, the original cell line this variant form was isolated from. In addition, these analyses show that the Δ148 is present in all cell lines examined, confirming the observation that this variant form of cyclin E is the major transcript found in these cells.

In order to apply the findings from culture studies to the in vivo condition, it was next determined whether the truncated cyclin E transcripts were also expressed in tumor tissue specimens. RT-PCR was performed using RNA isolated from seven paired samples of human breast carcinoma and normal adjacent tissue (NAT). For this experiment, primers flanking the entire coding region of cyclin E were used in order to detect all variants of cyclin E which could contain deletions in the coding region (primer L1CYCE having a nucleotide sequence as shown in SEQ ID NO:5 and primer R1CYCE having a nucleotide sequence as shown in SEQ ID NO:6). The RT-PCR products from NAT and tumor tissue samples ranged in size from 1.0 to 1.2 kb, which are consistent with products obtained with cultured breast cells. Surprisingly, not only did both NAT and tumor tissue samples express similar RT-PCR products corresponding to the cyclin E variants, but no distinct difference could be found among paired samples as the clinical stage of the disease increases. On the other hand, when whole cell lysates prepared from these tissue specimens were subjected to Western blot analysis, cyclin E protein alterations were observed which increased qualitatively and quantitatively as the stage of the disease increased. Western blot analysis of whole cell lysates (100 μg) were prepared from NAT and tumor tissue specimens and probed with a monoclonal antibody to cyclin E. Breast cancer types and histological/tumor grades were as follows: intraductal carcinoma of the breast, Stage T1,N0,M0, Grade I; invasive well differentiated ductal carcinoma, Stage T1,N0,M0, Grade I; intraductal carcinoma, Stage T1/2,N0,M0, Grade I; invasive and intraductal carcinoma,. Stage T2,N0,M0, Grade II; in situ and infiltrating ductal carcinoma, Stage T2,N1,M0, Grade II/III; infiltrating ductal carcinoma, Stage T3,N0,M0, Grade II/III; invasive ductal carcinoma, Stage 4,N0,M0, Grade III. In high staged tumor samples, an antibody to cyclin E reacted strongly with at least three overexpressed proteins ranging in size from 35 to 50 KDa, while in the NAT samples, one major protein of 50 KDa was present at very low levels, consistent with previous observations (Keyomarsi, et al., 1994). Collectively these observations suggest that at the level of RNA there are no apparent differences between normal and tumor cells or between tissue samples in their ability to express the alternate transcripts of cyclin E. However, the alteration in cyclin E protein observed exclusively in tumor cells, likely occurs post transcriptionally or translationally to result in various forms of the protein detected in tumor but not normal cells or tissues.

EXAMPLE 5

Cyclin E Truncated Variants Form Biochemically Active Complexes with cdk2.

Based on the evidence that multiple cyclin E transcripts are found in normal and tumor cells as well as in tissue samples, and that there is an active cyclin E/cdk2 protein complex present throughout the cell cycle of the MDA-MB-157 cell line, it was determined whether these alternate transcripts of cyclin E can give rise to a biochemically active product. To investigate this question, cyclin E and cdk2 were overexpressed in insect cells using the baculovirus expression system. Insect cells were co-infected with the recombinant baculovirus containing cdk2 and either cyclin E-wild-type, cyclin E-Δ9, or cyclin E Δ148 cDNAs. Following infection, cell extracts were collected, homogenized and subjected to Western blot and histone H1 kinase analysis. For Western blot analysis equal amounts (50 μg) of protein were added to each lane and the gel was then subjected to Western blot analysis with polyclonal antibody to cyclin E or to cdk2. A control lane corresponding to 50 μg of extracts from insect cells infected with either cyclin E wt alone, or cdk2 alone baculovirus was used. The results show that there were similar levels of expression of the three cyclin E variants and cdk2 in the infected sf9 cells within one day of infection and thereafter during the course of the experiment. Histone H1 kinase assays were also performed on the same cell extracts by immunoprecipitating equal amount of cell lysate with polyclonal antibody to cdk2 coupled to protein A beads using histone H1 as substrate. A control immunoprecipitate was performed with Normal Rabbit Serum in place of cdk2 antibody. H1 kinase analysis reveals that when the cyclin E-wt/cdk2 co-infected insect cell lysates were immunoprecipitated with an antibody to cdk2, the immunoprecipitates were capable of phosphorylating histone H1 within one day of infection and an active cyclin E/cdk2 complex persisted throughout the experiment. In insect cells co-infected with the two truncated variants of cyclin E, similar results were obtained illustrating that the complex which cycEΔ9 or cycEΔ148 formed with cdk2 is also active and is capable of phosphorylating histone H1. However a lower degree of activation was found compared to that with the cyclin E wild-type complex. There was a 2 fold difference in the ability of the cycEΔ9/cdk2 or cycEΔ148/cdk2 to phosphorylate histone H1 when compared to cyclin E wt/cdk2. These in vitro analyses suggest that once the cyclin E variant transcripts are translated, the protein products can give rise to a functionally active cyclin E complex capable of phosphorylating substrates such as histone H1.

EXAMPLE 6

Anti-sense Experiments

If cyclin E variant transcripts can only be translated in tumor but not normal cells, then these transcripts may be targeted therapeutically. Antisense RNA can be designed to cyclin E which would detect only Δ9 and Δ148 and not the wild-type forms and consequently inhibit their translation in tumor cells and not affect the normal cells. If Δ9 and Δ148 are biologically active and function to facilitate GLIS transition in tumor cells, then their inhibition would also cause inhibition of cell proliferation of tumor but not normal cells.

Analysis of RNA anti-sense therapeutics was initiated by using anti-sense oligos to the first 20 base pair sequence at the very N terminal region of the RNA which is present in all the cyclin E variants isolated to date. To ensure that the growth inhibition is due to inhibition of cyclin E translation and not due to non-specific anti-sense cytotoxicity, cyclin E sense oligos to the same region which the anti-sense RNA was designed to were also used.

Three different cell lines were used for the analysis: MCF-10A, a normal immortalized mammary epithelial cell line and two tumor cell lines, MDA-MB-157 and ZR75T. Exponentially growing cells were cultured in each well of a 24 well plate at a cell density of $1 \times 10^4$. 24–48 hours following plating, cells were treated with concentrations of cyclin E or D sense or anti-sense oligos. Sense and anti-sense cyclin E#1 and cyclin D were to base pairs 1–20; cyclin E#2 was to base pairs 10–30. Cells were treated for 9 days and culture media was removed every 3 days and replaced with fresh media containing fresh dilutions of the RNA oligos. Fresh sense or anti-sense RNA was added to the culture media every 72 hours to ensure against degradation of these RNA oligonucleotides which may be quite unstable at 37° C. if incubated longer than 3 days. Following 9 days of treatment, cells were washed three times, trypsinized and cell number quantitated electronically using a Coulter Counter. For each cell line 0 concentration was used as 0% growth inhibition and used for determination of growth inhibition of treated cells. Each condition was set up in duplicate wells and the experiment was repeated twice. These analyses reveal that at concentration range of 10–40 μM, both cyclin E and D anti-sense RNA are quite growth inhibitory against all cell lines examined. For example, 20 μM cyclin E anti-sense was sufficient to inhibit the growth of MDA-MB-157 by 65%, while the same concentration of sense oligo only inhibited 15% growth of cells. At 80 μM, both sense and anti-sense oligos had significant growth inhibitory activity against MDA-MB-157 cell line, most probably due to non-specific RNA oligo cytotoxicity. MCF-10A and ZR-75T cells on the other hand were quite resistant to the effects of non-specific cytotoxicity of RNA oligonucleotides as cyclin E sense concentration of 80 μM resulted in only negligible growth inhibition. The same concentrations of anti-sense oligos to cyclin E resulted in up to 70% and 40% growth inhibition, respectively. Similar results were obtained for each cell line with anti-sense oligos to both cyclin E and D. These analyses clearly demonstrate that anti-sense oligos against cell cycle regulatory proteins such as cyclins E or D can successfully inhibit the growth of these cells.

EXAMPLE 7

Biopanning of Monoclonal Antibodies With Bacteriophage Display Libraries

Scott and Smith (1990) presented a method of defining peptide ligands by using randomly synthesized peptide inserts in bacteriophage. Related methods were published by Cwirla et al. (1990) and by Devlin et al. (1990). Since that time a literature has arisen in which both the original hexapeptide inserts and larger inserts have been used in identifying epitopes recognized by monoclonal antibodies. This technique has great potential for the detection of critical epitopes within the truncated cyclin E protein forms and fragments thereof.

A well-balanced decapeptide (10-mer) library and a dodecapeptide (12-mer) library can be used (such as the dodecapeptide library available from Clontech Laboratories (Palo Alto, Calif.)). The libraries have both been constructed into a Fuse 5 vector (Scott and Smith 1990) by the insertion of a mixture of synthetic oligonucleotides, with the random decapeptides (or modified-random dodecapeptides) fused to the minor viral coat protein pIII of the bacteriophage. The libraries each have a complexity of approximately $3 \times 10^8$ independent clones, and a titer of $10^{12}$ to $10^{14}$ per ml.

The strategy for using these libraries largely follows the review recently presented by Scott (1992) and employs, with modifications, the detailed methodology for use of this system as described recently by Smith and Scott (1993). The strategy used is as follows.

Specifically, in the first round of biopanning a 60 mm streptavidin-coated petri dish is filled with blocking solution (0.5% BSA, 0.1 M $NaHCO_3$, 0.1 μg/ml streptavidin, 0.2% $NaN_3$) for 2 hours, then washed three times with TBS-0.5% Tween. Next, 1 μl of the library (about $1 \times 10^{11}$ phage) that has been incubated overnight at 4° C. with 1 μg of biotinylated Mab is diluted with 1 ml of TBS-Tween, and this mixture is then added to the petri dish and rocked for 15 minutes at room temperature. The petri dish is washed 10 times with TBS-Tween, and bound phage is eluted by pipetting 800 μl of 0.1 N HCl (pH adjusted to 2.2 with glycine) –1 mg/ml BSA into the dish. The eluate is then pipetted into a microfuge tube containing 48 μl of 2M Tris, to bring the pH up to about 8.

The eluate is concentrated and washed twice in TBS using an Amicon Centricon-30 filter (Amicon, Inc., Beverly, Mass.). This final product is titered out by making dilutions from a small amount of concentrated eluate in TBS-0.1% gelatin and adding 1 μl of each dilution made to 19 μl of TBS-gelatin, then adding 20 μl of starved K91 E. coli cells and incubating for 10 minutes at room temperature. After adding 200 μl of NZY medium containing 0.2 μg/ml tetracycline (Tc) and incubating at 37° C. for 1 hour, the mixture is plated out on NZY agar plates containing 40 μg/ml tetracycline and allowed to grow up overnight at 37° C.

After titering, the entire concentrated eluate from the first round of biopanning (about 50 μl) is added to an equal volume of fresh starved K91 cells, and amplification performed as described by Smith and Scott (1993). Following the first PEG/NaCl precipitation, the resulting pellet is dissolved in 1 ml TBS. Phage is then precipitated a second time with PEG/NaCl, allowed to stand at least 1 hour at 4° C., and the precipitate collected following centrifugation at 4° C. After careful removal of all the supernatant, the pellet is dissolved in 100 μl TBS. This amplified product can then be titered.

Second and third biopannings are carried out exactly as in the first, but using either an equal or a decreased amount of biotinylated Mab for each subsequent round, with 5 µl of amplified eluate. The second round of biopanning is concentrated and amplified as in the first round. The third round is stopped after eluting the bound phage from the petri dish. This eluate is not concentrated or amplified. Titerings are done before and after each round, and the percent yield is calculated as the number of bacteriophage obtained in an elution fraction relative to the initial number of bacteriophage (Christian et al. 1992). A yield should generally be greater than $10^{-5}$ to exceed background, with values of $10^{-4}$ to $10^{-1}$ typically observed. Increasing percent yields in subsequent rounds of biopanning are, in particular, suggestive that clones of increasing affinity are being selected.

In some experiments, an immunological screening assay, as described by Christian, et al. (1992) may be performed using NZY and Tc agar plates containing about 500 well-separated colonies. The colonies are transferred to nitrocellulose membrane filters (Biorad Laboratories, Hercules, Calif.), and the filters are immediately washed twice in TNT Buffer (10 mM Tris, pH 8.0, 150 mM NaCl, 0.05% Tween 20), blocked for 30 minutes at room temperature with gentle agitation in 20% normal goat serum in TNT buffer, then incubated for 2 hours at room temperature in primary Mab that has been diluted 1:1000 in blocking buffer. The filters are washed sequentially for 10 minutes at room temperature each wash, in washing buffer A (TNT Buffer+0.1% BSA), washing buffer B (TNT Buffer+0.1% BSA +0.1% NP-40), and then again washing buffer A, and incubated in a secondary peroxidase-conjugated goat anti-mouse IgG for 1½ hours at room temperature. The filters are washed as before, then put in a final wash of TN (10 mM Tris, pH. 7.5, 150 mM NaCl). Color development is observed after putting filters in ABTS substrate.

Small cultures of individual colonies are then grown up overnight, by either: a) selecting the colonies that were positive from the immunological screening; or b) skipping the screening step and randomly selecting colonies (about 100). Each colony is inoculated into 2 ml of NZY medium containing 20 µg/ml tetracycline, and these small cultures grown up overnight at 37° C., with vigorous shaking. The next day cultures are centrifuged to pellet the cells, and the supernatant is removed. To 1 ml of the supernatant is then added 150 µl PEG/NaCl, and the phage are precipitated overnight at 4° C. Following subsequent centrifugation and removal of supernatant, the pellet is dissolved in 1 ml TBS.

For DNA sequencing, 400 µl of the dissolved pellet is extracted once with phenol, and the resulting aqueous phase (about 300 µl) is added to 500 µl TE and 80 µl 3 M sodium acetate buffer. Then 1 ml ethanol-is added and the SS DNA is allowed to precipitate overnight at 4° C. Each sample is then microfuged for 30 minutes at 4° C., the DNA pellet washed once in 70% ETOH, dried, and resuspended in 7 µl $H_2O$. This template can be stored at −20° C. until ready to use.

Due to the quite GC-rich Sfi 1 cloning site flanking the insertion region, sequencing reactions can be carried out using the Sequenase 7-deaza dGTP DNA sequencing kit (Amersham-US Biochemicals, Arlington Heights, Ill.) with $^{32}$P-DATP and an antisense primer located approximately 40 nucleotides 3' to the insert site. Samples are run on a standard 6% sequencing gel using an IBI STS 45 sequencing apparatus (Eastman Kodak Company, Rochester, N.Y.).

The GCG software (Genetics Computer Group, Inc., Madison Wis.) is helpful for aligning sequences obtained from multiple clones in order to find consensus sequences.

At this point, an ELISA assay can be used to evaluate individual clones, if the number of clones is high. In brief, phage having undergone two PEG precipitations, and subsequently adjusted for titer, can be incubated overnight with biotinylated Mab, following which the mab-phage mixture can be added to wells of microtiter plates that have been previously coated with suitable immobilized target recognized by the mab. Following a series of washing steps, avidin-peroxidase is added, the wells washed again, chromogenic substrate added, and the wells eventually read on an ELISA plate reader. The relative decrease in strength of signal in this assay provides guidance as to the most promising clones for further study. Concensus peptides identified in this manner can be chemically synthesized and characterized with respect to ability to bind original antibody. Peptides showing high binding affinity for the antibody can then be used as immunogens in mice and/or rabbits.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Anderson, W. F. (1992). Science 256, 808–813.
Balass, M. et al., Proc Natl Acad Sci USA 90:10638–10642 (November 1993).
Band, V., & Sager, R. (1989). Proc. Natl. Acad. Sci. USA, 86, 1249–1253.
Berkner, K. L. (1988). BioTechniques 6, 616–629.
Bianchi, A. B., Fischer, S. M., Robles, A. I., Rinchik, E. M., & Conti, C. J. (1993). Oncogene, 8, 1127–1133.
Blackledge, J. A., et al. (1995). Annal Chem, 67, 843–848.
Anderson, W. F. (1992). Science 256, 808–813.
Buckley, M. F., Sweeney, K. J. E., Hamilton, J. A., Sini, R. L., Manning, D. L., Nicholson, R. I., deFazio, A., Watts, C. K. W., Musgrove, E. A., & Sutherland, R. L. (1993). Oncogene, 8, 2127–2133.
Capecchi, M. (1980). Cell 22, 479–488.
Cepko, C. (1988). Neuron 1, 345–353.
Christian, R. B. et al., J Mol Biol 227:711–718 (1992).
Claudio, T., et al. (1987). Science, 238, 1688–1694.
Claudio, T., et al., Cloning and transfer of acetylcholine receptor genes in: Molecular Neurobiology: A Short Course, McKay, R. D., Ed., Bethesda, Neuroscience Society, 22–27 (1984).
Crissman, H. A., & Tobey, R. A. (1974). Science, 184, 1287–1298.
Cwirla, S. E. et al., Proc Natl Acad Sci USA 87:6378–6382 (August 1990).
Devlin, J. J. et al., Science 249:404–406 (1990).
Draetta, G. F. (1994). Curr. Opin. Cell Biol., 6, 842–846.
Eglitis, M. A. and W. F. Anderson (1988). BioTechniques 6, 608–614.
Elledge, S. J., & Spottswood, M. R. (1991). EMBO J, 10, 2643–2659.
Evans, T., Rosenthal, E., Youngblom, J., Kistel, D., & Hunt, T. (1983). Cell, 33, 389–396.
Friedmann, T. (1989). Science 244, 1275–1281.
Gorman, C., DNA Cloning; A Practical Approach, Oxford, IRL Press, 143–190 (1985).

Hall, S. C., et al. (1993). *Proc Natl Acad Sci USA*, 90, 1927–1931.

Heichman, K. A., & Roberts, J. M. (1994). *Cell*, 79, 557–562.

Henzel, W. J., et al. (1993). *Proc Natl Acad Sci USA*, 90, 5011–5015.

Hinds, P. W., Dowdy, S. F., Eaton, E. N., Arnold, A., & Weinberg, R. A. (1994). *Proc. Natl. Acad. Sci*, 91, 709–713.

Hinds, P. W., Mittnacht, S., Dulic, V., Arnold, A., Reed, S. I., & Weinberg, R. A. (1992). *Cell*, 70, 993–1006.

Hobart, M. J. et al., Proc R Soc London B 252:157–162 (1993).

Hunter, T., & Pines, J. (1991). *Cell*, 66, 1071–1074.

Hunter, T., & Pines, J. (1994). *Cell*, 79, 573–582.

Jiang, W., Kahn, S. M., Tomita, N., Zhang, Y.-J., Lu, S.-H., & Weinstein, B. (1992). *Cancer Res.*, 52, 2980–2983.

Jiang, W., Kahn, S. M., Zhou, P., Zhang, Y.-J., Cacace, A. M., Infante, A. S., Doi, S., Santella, R. M., & Weinstein, I. B. (1993a). *Oncogene*, 8, 3447–3457.

Jiang, W., Zhang, Y.-J., Kahn, S. M., Hollstein, M. C., Santella, R. M., Lu, S.-H., Harris, C. C., Montesano, R., & Weinstein, I. B. (1993b). *Proc. Natl. Acad. Sci.*, 90, 9026–9030.

Joyce, G. F., Current Opinion in Structural Biology 4:331–336 (1994).

Keyomarsi, K., O'Leary, N., Molnar, G., Lees, E., Fingert, H. J., & Pardee, A. B. (1994). *Cancer Res.*, 54, 380–385.

Keyomarsi, K., & Pardee, A. B. (1993). *Proc. Natl. Acad. Sci. USA*, 90, 1112–1116.

Keyomarsi, K., Sandoval, L., Band, V., & Pardee, A. B. (1991). *Canc. Res.*, 51, 3602–3609.

King, R. W., Jackson, P. K., & Kirschner, M. W. (1994). *Cell*, 79, 563–571.

Klein, T. M., et al. (1987). *Nature* 327, 70–73.

Koff, A., Cross, F., Fisher, A., Schumacher, J., Leguellec, K., Philippe, M., & Roberts, J. M. (1991). *Cell*, 66, 1217–1228.

Lammie, G. A., Fantl, V., Smith, R., Shuuring, E., Brookes, S., Michalides, R., Dickson, C., Arnold, A., & Peters, G. (1991). *Oncogene*, 6, 439–444.

LaRocca, D. et al., Hybridoma 11:191–201 (1992).

Leach, S. F., Elledge, S. J., Sherr, C. J., Willson, J. K. V., Markowitz, S., Kinzler, K. W., & Vogelstein, B. (1993). *Cancer Res.*, 53, 1986–1989.

Lees, E., Faha, B., Dulic, V., Reed, S. I., & Harlow, E. (1992). *Genes Dev.*, 6, 1874–1855.

Lew, D. J., Dulic, V., & Reed, S. I. (1991). *Cell*, 66, 1197–1206.

Lopata, M. A., et al. (1984). *Nucl. Acids Res.*, 12, 5707.

Lovec, H., Sewing, A., Lucibello, F. C., Muller, R., & Möröy, T. (1994). *Oncogene*, 9, 323–326.

Maniatis et al., Molecular Cloning: A Laboratory Manual, Cold Spring Harbor Laboratory Press, Cold Spring Harbor, N.Y. (1982).

Mannino, R. J. and S. Gould-Fogerite (1988). *BioTechniques* 6, 682–690.

Matsushime, H., Roussel, M. F., Ashman, R. A., & Sherr, C. J. (1991). *Cell*, 65, 701–713.

Miller, L. K. (1989). *Bioessays* 11, 91–95.

Morgan, D. O. (1995). *Nature*, 374, 131–134.

Motokura, T., & Arnold, A. (1993). *Curr. Opin. Genet. & Devel.*, 3, 5–10.

Motokura, T., Bloom, T., Kim, H. G., Juppner, H., Ruderman, J. V., Kronenberg, H. M., & Arnold, A. (1991). *Nature*, 350, 512–515.

Mulligan, R. C. (1993). *Science* 260, 926–932.

Musgrove, E. A., Lee, C. S. L., Buckley, M. F., & R.L., S. (1994). *Proc. Natl. Acad. Sci.*, 91, 8022–8026.

Nurse, P. (1994). *Cell*, 79, 547–550.

Ohtsubo, M., & Roberts, J. M. (1993). *Science*, 259, 1908-1912.

Ohtsubo, M., Theodoras, A. M., Schumacher, J., Roberts, J. M., & Pagano, M. (1995). *Mol. Cell. Biol.*, 15, 2612–2624.

Parmley, S. F. and Smith, G. P., Gene 73:305–318 (1988).

Quelle, D. E., Ashmun, R. A., Shurleff, S. A., Kato, J.-y., Bar-Sagi, D., Roussel, M. F., & Sherr, C. J. (1993). *Genes & Dev.*, 7, 1559–1571.

Rao, P. N., & Johnson, R. T. (1970). *Nature*, 225, 159–164.

Rasmussen, H. H., et al. (1994). *Electrophoresis*, 15, 406–416.

Resnitzky, D., Gossen, M., Bujard, H., & Reed, S. I. (1994). *Mol. Cell. Biol.*, 14, 1669–1679.

Rosenberg, C. L., Kim, H. G., Shows, T. B., Kronenberg, H. M., & Arnold, A. (1991a). *Oncogene*, 6, 449–453.

Rosenberg, C. L., Wong, E., Pety, E. M., Bale, A. E., Tsujimoto, Y., Harris, N. L., & Arnold, A. (1991b). *Proc. Natl. Acad. Sci USA*, 88, 9638–9642.

Rosenwald, I. B., Lazaris-Karatzas, A., Sonenberg, N., & Schmidt, E. V. (1993). *Molec. Cell. Biol.*, 13, 7358–7363.

Sewing, A., Ronicke, V., Burger, C., Funk, M., & Muller, R. (1994). *J Cell Sci.*, 107, 581–588.

Scott, J. K., Trends in Biochem Sci 17:241–245 (1992).

Scott, J. K. and Smith, G. P., Science 249:386–390 (Jul. 27, 1990).

Sherr, C. J. (1993). *Cell*, 73, 1059–1065.

Sherr, C. J. (1994). *Cell*, 79, 551–555.

Shigekawa, K. and W. J. Dower (1988). *BioTechniques* 6, 742–751.

Smith, G. P. and Scott, J. K., Methods in Enzymology 217:228–257 (1993).

Soule, H. D., Maloney, T. M., Wolman, S. R., Peterson, W. D., Jr., Brenz, R., McGrath, C. M., Russo, J., Pauley, R. J., Jones, R. F., & Brooks, S. C. (1990). *Cancer Research*, 50, 6075–6086.

Standart, N., Minshull, J., Pines, J., & Hunt, T. (1987). *Dev. Biol.*, 124, 248–258.

"Stratagene Cloning Systems" C.atalog, Stratagene, LaJolla, Calif. (1993).

Studier, F. W., et al., "Use of T7 RNA Polymerase to Direct Expression of Cloned Genes," *Gene Expression Technology* vol. 185 (1990).

Swenson, K. I., Farrell, K. M., & Ruderman, J. V. (1986). *Cell*, 47, 861–870.

Verma, I. M. (1990). *Sci Am* 262, 68–84.

Wang, T. C., Cardiff, R. D., Zukerberg, L., Lees, E., Arnold, A., & Schmidt, E. V. (1994). *Nature*, 369, 669–671.

Wigler, M., et al. (1978). *Cell*, 14, 725.

Withers, D., Harvey, R., Faust, J., Melnyk, O., Carey, K., & Meeker, T. (1991). *Mol. Cell Biol.*, 11, 4846–4853.

Xiong, Y., Connolly, T., Futcher, B., & Beach, D. (1991). *Cell*, 65, 691–699.

What is claimed is:

1. An antibody or antigen binding fragment thereof, wherein said antibody or antigen binding fragment thereof is specific for a truncated human cyclin E selected from the group consisting of SEQ ID NO.9 and SEQ ID NO. 10, and wherein said antibody or antigen binding fragment thereof distinguishes between truncated human cyclin E protein and wild type human cyclin E.

2. The antibody of claim 1 wherein said antibody comprises a monoclonal antibody.

3. The antibody of claim 1 wherein said antibody comprises a polyclonal antibody.

* * * * *